US008039598B2

(12) United States Patent
Cao

(10) Patent No.: US 8,039,598 B2
(45) Date of Patent: Oct. 18, 2011

(54) MET FAB AND SCFV FRAGMENTS

(75) Inventor: Boliang Cao, Ada, MI (US)

(73) Assignee: Van Andel Research Institute, Grand Rapids, MI (US)

( * ) Notice: Subject to any disclaimer, the term of this patent is extended or adjusted under 35 U.S.C. 154(b) by 727 days.

(21) Appl. No.: 12/017,274

(22) Filed: Jan. 21, 2008

(65) Prior Publication Data

US 2009/0324603 A1    Dec. 31, 2009

Related U.S. Application Data

(60) Provisional application No. 60/885,786, filed on Jan. 19, 2007.

(51) Int. Cl.
C07K 16/28 (2006.01)
C07K 16/00 (2006.01)
A61K 39/395 (2006.01)
G01N 33/53 (2006.01)

(52) U.S. Cl. ............ 530/388.22; 530/387.1; 530/388.1; 530/388.15; 424/130.1; 424/135.1; 424/141.1; 424/142.1; 424/143.1; 435/7.1

(58) Field of Classification Search .................. None
See application file for complete search history.

(56) References Cited

OTHER PUBLICATIONS

Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
Watkins, N. A, et al. "Single-chain antibody fragments derived from a human synthetic phage-display library bind thrombospondin and inhibit sickle cell adhesion". Blood. 102(2): 718-24 (Jul. 15, 2003).
Weiner, L., et al. "Tunable antibodies". Nature Biotech 23(5): 556-557 (May 2005).
Weissleder, R., et al. "In vivo imaging of tumors with protease-activated near-infrared fluorescent probes". Nature Biotech. 17: 375-378 (1999).
Wilson, I. A. et al. "Antibody-antigen interactions: new structures and new conformational changes". Curr. Opin. Struct. Biol. 4: 857-867 (1994).
Wu, A.M., et al. "Arming antibodies: prospects and challenges for immunoconjugates". Nature Biotech 23:1137-46 (Sep. 2005).
Zemlin, M., et al. "Expressed Murine and Human CDR-H3 Intervals of Equal Length Exhibit Distinct Repertoires that Differ in their Amino Acid Composition and Predicted Range of Structures". J. Mol. Biol. 334: 733-749 (2003).
Program and Abstracts, Ninth Conference on Cancer Therapy with Antibodies and Immunoconjugates. Cancer Biotherapy & Radiopharmaceuticals 17:465-494 (2002).
Huls, G. et al. "Tumor cell killing by in vitro affinity-matured recombinant human monoclonal antibodies". Cancer Immunol Immunother 50: 163-171 (2001).
Gura, T. "Magic Bullets hit the target". Nature 417: 584-586 (Jun. 6, 2002).
Adams, G., et al, "High Affinity Restricts the Localization and Tumor Penetration of Single-Chain Fv Antibody Molecules". Cancer Res. 61: 4750-4755 (Jun. 15, 2001).
Altschul, S., et al. "Gapped BLAST and PSI-BLAST: a new generation of protein database search programs". Nucleic Acids Res. 25 (No. 17): 3389-3402 (1997).
Baneyx, F., et al. "Recombinant protein folding and misfolding in Escherichia coli". Nature Biotech. 22: 1399-1408 (Nov. 2004).
Batzer, M., et al. "Enhanced evolutionary PCR using oligonucleotides with inosine at the 3'sterminus". Nucleic Acid Res. 19: 5081 (1991).
Begent, RH., et al. "Clinical evidence of efficient tumor targeting based on single-chain Fv antibody selected from a combinatorial library". Nat Med. 2: 979-984 (Sep. 1996).
Berzofsky, J., et al. "Antibody-Antigen Interactions and Monoclonal Antibodies". Fundamental Immunology Paul, W E , Ed , Raven Press New York, N Y (1984).
Birchmeier, C., et al. "Met, Metastasis, Motility and More". Nat. Rev. Mol. Cell Biol. 4: 915-925 (Dec. 2003).
Bird, R., et al. "Single-Chain Antigen-Binding Proteins". Science 242: 423-426 (Oct. 21, 1988).
Bruchez, M., et al. "Semiconductor Nanocrystals as Fluorescent Biological Labels". Science 281: 2013-2016 (Sep. 25, 1998).
Cao, B., et al. "Neutralizing monoclonal antibodies to hepatocyte growth factor/scatter factor (HGF/SF) display antitumor activity in animal models". Proc. Natl. Acad. Sci. USA 98: 7443-7448 (Jun. 19, 2001).
Chan, W., et al. Quantum Dot Bioconjugates for Ultrasensitive Nonisotopic Detection. Science 281: 2016-2018 (1998).
Devereux, J., et al. "A comprehensive set of sequence analysis programs for the VAX". Nucleic Acids Res. 12 (1): 387-395 (1984).
Groner, B., et al. "Therapeutic Antibodies". Current Molecular Medicine 4: 539-547 (2004).
Guillemard, V., et al. "Prodrug chemotherapeutics bypass p-glycoprotein resistance and kill tumors in vivo with high efficacy and target-dependent selectivity". Oncogene 23: 3613-3621 (Mar. 22, 2004).
Guillemard, V., et al. "Taxane-Antibody Conjugates Afford Potent Cytotoxicity, Enhanced Solubility, and Tumor Target Selectivity". Cancer Res 61: 694-699 (Jan. 15, 2001). Heitner, T., et al. "Selection of cell binding and internalizing epidermal growth factor receptor antibodies from a phage display library". J. Immunol. Methods. 248: 17-30 (2001).
Holliger, P., et al. "Engineered antibody fragments and the rise of single domains". Nature Biotechnology 23: 1126-36 (Sep. 2005).
Hoogenboom, H.R. "Designing and optimizing library selection strategies for generating high-affinity antibodies". Trends Biotechnol. 15: 62-70 (Feb. 1997).
Hudson, P.J., et al. "Engineered Antibodies". Nat Med. 9: 129-34 (Jan. 2003).

(Continued)

*Primary Examiner* — Sharon Wen

(74) *Attorney, Agent, or Firm* — Douglas H. Siegel; Honigman Miller Shwartz & Cohn LLP

(57) ABSTRACT

Antibody fragments (Fabs and scFvs) specific to the Met receptor are disclosed. Compositions and kits including these Fabs and scFvs, and drug and imaging conjugates of these Fabs and scFvs also are disclosed. The novel Fabs and scFvs can be internalized into the interior of a cell. Methods include using the novel Met Fabs and scFvs for diagnosing, prognosing, and treating cancer, and for evaluating chemotherapeutic response.

22 Claims, 8 Drawing Sheets

OTHER PUBLICATIONS

Huls, G.A. et al. "A recombinant, fully human monoclonal antibody with antitumor activity constructed from phage-displayed antibody fragments". Nat Biotechnol.17: 276-81 (Mar. 1999).

Huston, J., et al. "Protein engineering of antibody binding sites: Recovery of specific activity in an anti-digoxin single-chain Fv analogue produced in *Escherichia coli*". Proc. Natl. Acad. Sci. USA 85: 5879-5883 (Aug. 1988).

Iyer, M., et al. 8-[18F] Fluoropenciclovir: An Improved Reporter Probe for Imaging HSV1-tk Reporter Gene Expression In Vivo Using PET. J Nucl Med 42: 96-105 (Jan. 2001).

Jakobovits, A., "Production of fully human antibodies by transgenic mice". Curr Opin Biotechnol 6: 561-566 (1995).

Jones PT., et al. "Replacing the complementarity-determining regions in human antibody with those from a mouse". Nature 321: 522-525 (1986).

Karlin, S., et al. "Applications and statistics for multiple high-scoring segments in molecular sequences". Proc. Natl. Acad. Sci. USA 90: 5873-5877 (Jun. 1993).

Kohler, G., et al. "Continuous cultures of fused cells secreting antibody of predefined specificity". Nature 256: 495-497 (Aug. 7, 1975).

Kohls, M., et al. "Mab-Zap: A Tool for Evaluating Anitbody Efficacy for Use in an Immunotoxin". Biotechniques 28: 162-165 (Jan. 2000).

Lee, C., et al. "High-affinity Human Anitbodies from Phage-displayed Synthetic Fab Libraries with a Single Framework Scaffold". J. Mol. Biol. 340: 1073-1093 (2004).

Liu, B., et al. "Mapping Tumor Epitope Space by Direct Selection of Single-Chain Fv Antibody Libraries on Prostate Cancer Cells". Cancer Res. 64: 704-710 (Jan. 15, 2004).

Liu, Y., et al. "Recombinant Single-Chain Antibody Fusion Construct Targeting Human Melanoma Cells and Containing Tumor Necrosis Factor". Int J Cancer 108: 549-557 (2004).

Lu, J., et al. "An alternating selection strategy for cloning phage display antibodies". Journal of Immunological Methods 228: 109-119 (1999).

Lui, V.W., et al. "EGFR-Mediated Cell Cycle Regulation". Anticancer Res. 22: 1-11 (2002).

Mamot C., et al. "Epidermal Growth Factor Receptor-Targeted Immunoliposomes Significantly Enhance the Efficacy of Multiple Anticancer Drugs In vivo". Cancer Res 65: 11631-11638 (Dec. 15, 2005).

Nguyen, T. H., et al. "Improved gene transfer selectivity to hepatocarcinoma cells by retrovirus vector displaying single-chain variable fragment antibody against c-Met". Cancer Gene Ther. 10: 840-849 (2003).

Ohashi, K., et al. "Sustained survival of human hepatocytes in mice: A model for in vivo infection with human hepatitis B and hepatitis delta viruses". Nat. Med. 6: 327-331 (Mar. 2000).

Ohtsuka, E., et al. "An Alternative Approach to Deoxyoligonucleotides as Hybridization Probes by Insertion of Deoxyinosine at Ambiguous Codon Positions". J. Biol. Chem. 260: 2605-2608 (Mar. 10, 1985).

Pearson, W.R., et al. "Improved tools for biological sequence comparison". Proc. Nat'l. Acad. Sci 85: 2444-2448 (Apr. 1988).

Popkov, M., et al. "Targeting Tumor Angiogenesis with Adenovirus-Delivered Anti-Tie-2 Intrabody". Cancer Res. 65: 972-81 (Feb. 1, 2005).

Reichert, J.M., et al. "Monoclonal antibody successes in the clinic". Nature Biotechnology 23:1073-1078 (Sep. 2005).

Rossolini, G., et al. "Use of deoxyinosine-containing primers vs degenerate primers for polymerase chain reaction based on ambiguous sequence information". Mol. Cell. Probes 8: 91-98 (1994).

Rothlisberger, D., et al. "Domain Interactions in the Fab Fragment: A Comparative Evaluation of the Single-chain Fv and Fab Format Engineered with Variable Domains of Different Stability". J Mol Biol, 347: 773-789 (2005).

Rousselet N, et al. "Inhibition of Tumorigenicity and Metastasis of Human Melanoma Cells by Anti-Cathepsin L Single Chain Variable Fragment". Cancer Res. 64: 146-51 (Jan. 1, 2004).

Scheffer, G.L., et al. "Selection and characterisation of a phage-displayed human antibody (Fab) reactive to the lung resistance-related major vault protein". Br J Cancer, 86: 954-962 (2002).

Schrama D, et al. "Antibody targeted drugs as cancer therapeutics". Nature Reviews of Drug Discovery 5: 147-159 (Feb. 2006).

Souriau, C. et al. "Human Antibody Fragments Specific for the Epidermal Growth Factor Receptor Selected from Large Non-immunised Phage Display Libraries". Growth Factor, 22(3):185-194 (Sep. 2004).

Torelli, A. et al. "ADVANCE and ADAM: two algorithms for the analysis of global similarity between homologous informational sequences". Comput. Appl. Biosci. 10: 3-5 (1994).

Vallabhajosula, S. "Radiopharmaceuticals in Oncology" In: Nuclear Oncology. I Khalkhali et al., eds. Lippincott Williams & Wilkins, Philadelphia, PA. pp. 31-62 (2001).

Von Mehren, M., et al. "Monoclonal Antibody Therapy for Cancer". Annu Rev Med 54: 343-69 (2003).

Van Osdol, W., et al. An Analysis of Monoclonal Antibody Distribution in Microscopic Tumor Nodules: Consequences of a 'Binding Site Barrier'. Cancer Res. 51: 4776-4784 (Sep. 15, 1991).

Ward, E., et al. "Binding activities of a repertoire of single immunoglobulin variable domains secreted from *Escherichia coli*". Nature 341: 544-546 (1989).

Jiao, Yongjun et al., "Construction of Human Naive Fab Library and Characterization of Anti-Met Fab Fragment Generated From the Library". Molecular Biotechnology 31, 41-54 (2005).

* cited by examiner

MET FAB AND SCFV FRAGMENTS

CROSS-REFERENCE TO RELATED APPLICATION

This application claims the benefit of provisional U.S. Patent Application Ser. No. 60/885,786, filed on Jan. 19, 2007, which is herein incorporated by reference in its entirety.

FIELD OF THE INVENTION

This invention in the field of molecular biology, immunology, and cancer diagnosis and therapy, is directed to monoclonal antibody (mAb) compositions that are useful for imaging and treating tumors that express the c-met proto-oncogene product "c-Met" (or "Met"), a receptor protein tyrosine kinase.

BACKGROUND OF THE INVENTION c-Met is a receptor protein tyrosine kinase of the same family as epidermal growth factor (EGF) receptors. This transmembrane protein acts as the cell surface membrane receptor in which the extracellular domain (ECD) binds hepatocyte growth factor/scatter factor (HGF/SF, also abbreviated HGF herein). c-Met, used interchangeably with "Met", is a disulfide-linked heterodimer with $\alpha$ ($M_r$ 45,000) and $\beta$ ($M_r$ 145,000) subunits. The $\alpha$ chain is located outside the cell membrane, whereas the $\beta$ chain consists of an extracellular domain, a single transmembrane domain, and a cytoplasmic moiety in which the receptor tyrosine kinase domain resides (Birchmeier, C., et al. (2003) *Nat. Rev. Mol. Cell Biol.* 4, 915-925). c-Met dimerizes after binding ligand to form the active kinase. The intracellular tyrosine kinase domain activates a complex cascade of biochemical reactions. The c-Met receptor kinase regulates cellular proliferation, migration, differentiation and branching morphogenesis during development and homeostasis.

c-Met is also expressed on the cell surface of a variety of human primary solid tumors and in their metastases (http://www.vai.org/met/). In its activated state, the c-Met receptor controls growth, invasion, and metastasis of cancer cells through multiple signal transduction pathways. In some cancer cell lines, loss of c-Met expression through silencing promotes apoptosis, demonstrating that c-Met is necessary for survival. Met activity increases through mutations in the kinase or juxtamembrane domains, through overexpression, or through binding to HGF. In addition to increased c-Met expression, elevated HGF/SF concentrations in the tumor microenvironment have also been associated with adverse outcome. For example hypoxic tumor stromal cells in pancreatic cancer increase HGF secretion and accelerate pancreatic cancer progression.

c-Met is one of the most frequently genetically altered or otherwise dysregulated receptor tyrosine kinases (RTK) in advanced human cancers and thus represents an attractive treatment target. Kinase activating c-Met mutations are observed in sporadic renal, lung, head and neck, hepatocellular carcinoma, non small cell lung cancer (NSCLC), gastric cancer and melanoma. Furthermore, amplification of the c-Met locus has been detected in gastric, metastatic colorectal and esophageal adenocarcinoma, additional c-Met-related diseases. Activation of c-Met in cancer cells induces the secretion of angiogenic factors, such as VEGFA and IL-8 and inhibits synthesis of thrombospondin-1, an anti-angiogenic factor. In addition, c-Met activation in endothelial cells causes angiogenesis. While the cytotoxic effects of inhibiting Met activity may only occur in cancers with activated c-Met, the antiangiogenic effect may exist more frequently. Any disease associated with Met expression is referred to herein as a "Met-related disease".

The magnitude of c-Met expression predicts the aggressiveness of a number of cancer types (http://www.vai.org/met/). Accurate detection and quantification of c-Met protein expression are needed to identify cancers that are likely responsive to c-Met inhibitors and the development of such molecular diagnostics lags significantly behind the drug development.

Antibody molecules and their derivatives have tremendous potential for use in a variety of research, diagnostic, and therapeutic applications. To provide targeting specificity, it is useful to develop a targeted cancer therapeutic by generating a ligand that specifically binds to a receptor which is tumor specific or sufficiently over-expressed in the tumor (Scheffer, et al. (2002) *Br J Cancer,* 86:954-962; Gura, T. (2002) *Nature,* 417: 584-586; Popkov, M., et al. (2005) *Cancer Res.* 65: 972-81; Wilson, I. A. et al. (1994). *Curr. Opin. Struct. Biol.* 4, 857-867; Weiner, L. et al. (2005) *Nature Biotech* 23, 556-557). Antibodies have proven to be important targeting ligands for cell surface receptors. Recent progress in the manipulation of antibody subunits using molecular techniques, plus the ability to reproducibly select an antibody, an antibody fragment, or a peptide, allows the generation of useful binding subunits, while avoiding many of the problems that have often been associated with these molecules.

All antibodies are immunoglobulin (Ig) molecules made up of two heavy (H) and two light (L) chains. Each H and L chain are linked by a disulfide bridge which is just N-terminal of a "hinge" region. Pairs of two chains, disulfide linked, include the same basic unit of four polypeptide chains: two light chains (L) and two heavy chains (H). Both the heavy chains and light chains have intra-chain disulfide bridges, which create polypeptide loops or domains, of about 110 amino acids. These domains are referred to as VH (variable domain of the H chain), VL (variable domain of the L chain), CH1, CH2, CH3 (constant domains of the H chain), and CL (constant domain of the L chain). An Fab fragment was originally defined as is a papain digestion product of an intact antibody made of the N-terminal "half" of the H-chain which is now defined as VH-CH1 and all of the L-chain which is now defined as VL-CL. The Fab fragment contains the antigen binding site defined by the VH and VL domains of the H and L chains, respectively. Hence, the antigen binding site of any antibody (or antigen binding fragment thereof) is made up of the V domains (VH and VL) that interact physically with one another. When physically associated, these domains together are also referred to as an Fv fragment, while recombinant forms of these domains in the form of a single chain are referred to as single chain Fv fragments (scFv).

The term "CDR" refers to the complementarity determining region or hypervariable region amino acid residues of an antibody which are responsible for antigen-binding. Framework or "FR" amino acid residues are those variable domain residues other than and bracketing the CDR regions. The variable (V) domain of an Ig chain includes hypervariable (HV) regions which are also known as complementarity-determining regions (CDRs) because they are important in "determining" the structure of the antibody combining site that is complementary the epitope bound. Each H and L chain V region has three HVs or CDRs. The segments on either side of each HV region which are relatively invariant are termed "framework regions" (FRs). Thus, the order of these regions in a V domain (from the N-terminus) is as follows: FR1-HV1-FR2-HV2-FR3-HV3-FR4. For example, the three HV regions are roughly from residues 28-35, 49-59 and 92-103, respectively. The framework regions form the β-sheets that provide the structural framework of the domain, with the HV sequences corresponding to three loops at one edge of each sheet that are juxtaposed in the folded protein. The HV loops from the VH and VL domains are brought together, creating a single HV site at the tip of the Fab fragment which forms the antigen binding site. (See, for example, Janeway, C. A., Jr. et al., IMMUNOBIOLOGY, 2n ed., Garland Publishing Inc., New York, 1996, chapter 3).

One antigen validated for raising antibodies is c-Met. Mouse mAbs against human c-Met and against human HGF/SF have been generated (Ohashi, K., et al. (2000) *Nat. Med.* 6, 327-331; Cao, B., et al. (2001) *Proc. Natl. Acad. Sci. USA* 98, 7443-7448; Nguyen, T. H., et al. (2003) *Cancer Gene Ther.* 10, 840-849), and some of them showed strong affinities both in vitro and in animal models. However, clinical problems resulting from the formation of human antimurine antibodies and other pharmacodynamic effects have hampered their efficacy in the human body.

The mechanism by which antibodies produce therapeutic outcomes include antibody dependent cellular cytotoxicity (ADCC), complement-mediated cytotoxicity, and the blocking of signal pathways that promote uncontrolled cell proliferation, e.g., with a neutralizing antibody (Von Mehren M, et al. *Annu Rev Med* 54:343-69 (2003)).

Antibodies are good delivery vehicles for targeting agents for treatment or in vivo diagnosis. Antibodies can be conjugated to a compound (e.g., a nucleic acid, chemotherapy compound, toxin, or radionuclide) to direct such compound to cancer cells by recognizing the specific tumor marker on the cell surface. Antibody-conjugated drug, consisting of antibodies coupled to toxins or chemicals, are extremely useful tools in the elimination of specific cell populations in vitro and in vivo for research and therapeutic applications. The antibody is used to target the drug to a specific cell population, which is distinguished by its cell-surface antigen (Groner, B., et al. (2004), *Current Molecular Medicine* 4, 539-547; Watkins N A, et al. (2003) *Blood.* 102:718-24; Rousselet N, et al. (2004) *Cancer Res.* 64: 146-51). This can be done by conjugating chemotherapeutic drugs, radionuclides, or immunoliposomes for nanoscale delivery, and by directly fusing the antibody to an immunotoxin or cytokines using recombinant technology (Wu A M, et al. *Nature Biotech* 23:1137-46 (2005); Mamot C, et al. *Cancer Res* 65:11631-38 (2005)). An antibody-conjugated drug delivery system can direct toxic compounds to penetrate the targeted malignant tissue or cells specifically, thus decreasing the toxicity of drug to normal cells nearby and elsewhere, and increase the therapeutic effect by enhancing the accumulated dose of the drug in the targeted tissue. Antibody conjugates eliminate damage that otherwise would be caused to normal cells if such compounds were delivered to a patient by traditional chemotherapy regimens (Schrama D, et al. (2006) *Nature Reviews of Drug Discovery* 5: 147-159).

Beside the conjugation of chemotherapeutics, radionuclides or toxins, antibody conjugates have been developed in many fields, including the antibody-cytokine fusion protein for immune modulation treatment, antibody-ligand fusion protein for apoptosis induction, and the antibody directed enzyme pro-drug targeting (ADEPT).

Conjugation also increases the solubility of some compounds in physiological solutions, enhancing the stability of the compounds, and preventing the conjugated drug from being pumped out of cells by the multidrug resistance associated p-glycoprotein transmembrane pump (Guillemard V, et al. *Cancer Res* 61: 694-9 (2001); Guillemard H, et al. *Oncogene* 23:3613-21 (2004)).

When using an antibody for drug delivery, internalization of the antibody is generally desired since it allows some compounds to be delivered intracellularly, for example after release, from the antibody. For the purpose of chemoimmunoconjugation, an antibody that can be endocytosed by a cell is essential since an internalized antibody can lead the conjugated molecules into the cells to accumulate. Some linkers of the conjugation also need to be internalized to release the compounds by the lysosome (Schrama D, et al. (2006) *Nature Reviews of Drug Discovery* 5: 147-159).

An antibody conjugated to a detectable label such as a radionuclide provides a method for early diagnosis of a malignancy, when a cell surface protein is overexpressed or mutated so that it is distinguishable by an antibody from the unmutated form. Established methods for radiolabeling mAbs in suitable quantity and of appropriate quantity for scintigraphy are available, feasible, relatively inexpensive, and adaptable to virtually any mAb regardless of its epitopic specificity. New radiolabeling methods are continually emerging, and many laboratories are evaluating a wide range of antibody derivatives—from full-length chimeric and humanized molecules, to monomeric and multimeric antibody fragments, to immunoconjugates—as potentially superior imaging and therapeutic agents, with improved targeting selectivity and more favorable biological turnover kinetics (Program and Abstracts, Ninth Conference on Cancer Therapy with Antibodies and Immunoconjugates. 2002. Cancer Biotherapy & Radiopharmaceuticals 17:465-494).

Moreover, the reagents, supplies, and equipment required to perform radioimmunoscintigraphy in experimental animals and in humans are commonplace. For decades decommissioned or refurbished clinical gamma cameras have proven satisfactory for animal imaging applications, and they continue to do so. Modified or custom-built gamma cameras adapted for small animal imaging are becoming more widely available.

The major advantage of scintigraphy as a molecular imaging modality (not limited to imaging with antibodies) is that the acquired images are inherently quantitative. The physics of gamma radiation and the mathematical analysis of nuclear images, including corrections for photon attenuation and other artifacts, are well understood. In animal models, as well as in human studies, one can noninvasively and accurately measure net accumulation and some kinetic parameters of radiopharmaceutical interactions with target lesions, and the concurrent collection of even a small set of biological samples (e.g., blood and excreta) for direct counting combined with quantitative analysis of diagnostic images enables one to make useful dosimetry estimates for therapeutic purposes.

Many different radiopharmaceuticals are available for imaging neoplasms. They range from classical agents such as sodium iodide ($Na^{131I}$, thallium chloride ($^{201}TlCl$), and gallium citrate ($^{67}Ga$-citrate) to highly selective positron-emitting reporter gene detection systems (Vallabhajosula S (2001) *Nuclear Oncology*; I Khalkhali et al., eds. Lippincott Williams & Wilkins, Philadelphia, Pa. pp. 31-62; Iyer M et al. (2001) *J Nucl Med* 42, 96-105). Radiolabeled molecules that bind to specific cell surface components provide one successful approach to tumor imaging and therapy. Examples are OCTREOSCAN® for imaging and potentially treating neuroendocrine neoplasms, CEASCAN® and ONCOSCINT® for imaging colorectal and ovarian cancers, and BEXXAR® and ZEVALIN® for detecting and treating certain lymphomas.

Relatively smaller antibody fragments have higher penetrating speed into the solid tumor tissue (Holliger P, et al. *Nature Biotechnology* 23: 1126-36 (2005)), plus, if they are xenogeneic to the host, they have fewer foreign epitopes that can be recognized by the recipient's immune system. To avoid such immunogenic effects of xenoantibodies, most antibodies in clinical trials or use are human antibodies or at least chimeric (and humanized) antibodies so that they comprise a human constant regions linked to the original, xenogeneic (typically murine) variable regions.

Not all antibodies are suitable for creating a therapeutic drug, and large numbers of antibodies may need to be screened. This is a time-consuming and expensive process if each potential candidate must be conjugated to the drug and purified (Hudson P J, et al. (2003) *Nat Med.* 9:129-34; Kohls, M. et al., (2000) *Biotechniques,* 28: 162-165.

Since the 1970s, rodent antibodies have been widely applied for medical purposes, and mainly for in vitro diagnosis (Kohler G, et al (1975 Nature 256:495-497). The first therapeutic murine mAbs clinical study was performed in the early 1980s, but failed due to human anti-mouse antibodies (HAMA), short serum half-lives, and low efficacy of interaction with human immune effector cells (Reichert J M, et al (2005) *Nature Biotechnology* 23:1073-1078). However, completely human antibody fragments can be used to minimize the regions of non-human origin and thereby increase clinical tolerance. (Liu, Y., et al (2004) *Int J Cancer* 108, 549-557; Adams, G., et (2001) *Cancer Res.* 61: 4750-4755; Souriau, C. et al. (2004) *Growth Factor,* 22(3):185-194; Lui, V. W. et al (2002) *Anticancer Res.* 22, 1-11).

Human antibodies are desired for treatment and in vivo diagnosis of patients in order to prevent the HAMA response that could eliminate non-human antibodies and thus decrease the effect of the non-human antibodies after the first use. The development of recombinant technologies make it possible to generate a chimeric antibody (combining the variable region of a mouse and the constant region of human) or a fully human antibody for clinical use. Currently, three kinds of technologies have been developed to make a fully human antibody: a fully human antibody raised by a transgenic mouse (Jakobovits A (1995) *Curr Opin Biotechnol* 6: 561-566), humanization of a murine antibody (Jones P T, et al (1986) *Nature* 321: 522-525), and panning of recombinant human antibody libraries.

There are numerous reports of human antibodies successfully raised from combinatorial libraries that are representative of the natural immune response (Huls, G. et (2001) *Intl Cancer Res.* 50, 163-171; Huls, G A, et al (1999) *Nat Biotechnol.* 17:276-81; Begent R H, et al. (1996) *Nat Med.* 2:979-984; Liu, B., et al. (2004) *Cancer Res.* 64: 704-710; Scheffer G L, et al. (2002) *Br J Cancar,* 86:954-962; Hudson P J, et al. (2003) *Nat Med.* 9:129-34).

Using phages to display non-immunized libraries consisting of large numbers of IgG fragments, Fab fragments or scFvs for specific antigens have been recovered. But the antibodies fragments from these libraries often have weak affinities (in the range of $10^{-6}$ M). Phage display of antibody combinatorial libraries not only creates the direct physical linkage between genotype and phenotype that exists for B lymphocytes, but can also mimic in vitro many of the in vivo processes which result in the production of high-affinity Abs (Huls, G, et al. (2001) *Intl Cancer Res.* 50, 163-171; Huls G A, et al. (1999) *Nat Biotechnol.* 17:276-81).

Because c-Met is overexpressed in solid tumors, c-Met is an ideal target for antibody-directed drug delivery and for tumor imaging. To achieve this aim, a human anti-Met antibody, antibody Fab fragment, or scFv fragment is desired.

SUMMARY OF THE INVENTION

The present invention includes a functional Met-specific single chain Fv (scFv) antibody fragment with a high affinity for Met, and a functional Met-specific Fab fragment with a high affinity for Met. For clinical application as targeting moiety, the novel anti-Met scFv and anti-Met Fab fragments have appreciable antigen binding properties and rapid internalization upon antigen binding.

More specifically, the present invention includes Met monoclonal antibodies and antibody fragments Fab-Met-2 and scFv-S1, and antigen-binding fragments thereof, produced by the bacterial strains deposited as Patent Deposit Designation PTA-7897 and PTA-7898, respectively, in the American Type Culture Collection, 10801 University Blvd., Manassas, Va. 20110-2209, a recognized public depository for strains of microorganisms, having been deposited on Sep. 22, 2006. The present invention further includes a conjugate having either an imaging agent or a drug conjugated to these fragments. An anti-Met mAb, Fab, scFv, or other fragment or functional derivative described herein may also be referred to herein as a "Met mAb", "Met Fab", "Met scFv", etc.

Further, the present invention includes a composition comprising an antigen-binding fragment produced by the bacterial strain deposited in the American Type Culture Collection under Patent Deposit Designation ATCC PTA-7897, or a functional derivative of this fragment, and also includes conjugating either an imaging agent or a drug to this fragment. The present invention also includes a composition comprising an antigen-binding fragment produced by the bacterial strain deposited in the American Type Culture Collection under Patent Deposit Designation PTA-7898, or a functional derivative of this fragment, and also includes conjugating either an imaging agent or a drug to this fragment.

The present invention also includes a human monoclonal antibody or antigen-binding fragment that binds specifically to Met, wherein the antibody or fragment comprises 5-20 contiguous residues of SEQ ID NO: 3, or 5-20 contiguous residues of SEQ ID No. 4; or wherein the amino acid sequence of the heavy chain variable region the antibody or fragment comprises 5-20 contiguous amino acid residues of SEQ ID No. 6 and the light chain variable region the antibody or fragment comprises 5-20 contiguous amino acid residues of SEQ ID No. 6.

Another embodiment of the invention includes an isolated nucleic acid comprising a nucleotide sequence of SEQ ID Nos. 1, 2, or 5, or conservatively modified variants thereof.

Methods of the present invention include inhibiting cell proliferation, inhibiting metastasis, or reversing neoplastic growth in cells that express Met receptors, comprising administering one of the above-described novel antibodies, fragments, or functional derivatives to a subject. Other methods of the present invention include diagnosing or prognosing a Met-related disease by administering to a patient one of the above-described novel antibodies, fragments, or functional derivatives. Additionally, a method of the present invention includes evaluating the chemotherapeutic response of a patient having a Met-related cancer by administering to the patient one of the above-described novel antibodies, fragments, or functional derivatives.

A further embodiment of the present invention is an isolated cell line that produces one of the above-described novel antibodies, fragments, or functional derivatives. In one embodiment, the isolated cell line is the bacterial strain deposited in the American Type Culture Collection under Patent Deposit Designation ATCC PTA-7897 or the bacterial strain deposited in the American Type Culture Collection under Patent Deposit Designation ATCC PTA-7898.

The present invention also includes a vector comprising one of the above-described novel nucleic acid molecules. Further, the vector may also include an expression control sequence operably linked to the nucleic acid molecule. In another embodiment, the invention is (1) a host cell comprising this vector, wherein the host cell expresses the nucleic acid molecule, or (2) a non-human transgenic animal or transgenic plant which expresses one of the above-described novel nucleic acid molecules.

Also, the present invention includes a method for producing an anti-Met antibody or antigen-binding fragment thereof, comprising culturing the above-described novel host cell or cell line under suitable conditions and recovering said antibody or fragment.

Finally, another embodiment of the present invention is a kit, including: a first container, a label on the container, and a composition contained within the container, wherein the composition includes an active agent effective for treating cancer, the label on the container indicates that the composition can be used for treating cancer, and the active agent in the composition comprises one of the above-described monoclonal antibodies or an antigen-binding fragments; a second container comprising a pharmaceutically-acceptable buffer; and instructions for using the antibody or fragment thereof to treat cancer.

DETAILED DESCRIPTION OF THE PREFERRED EMBODIMENTS

Figure 1:
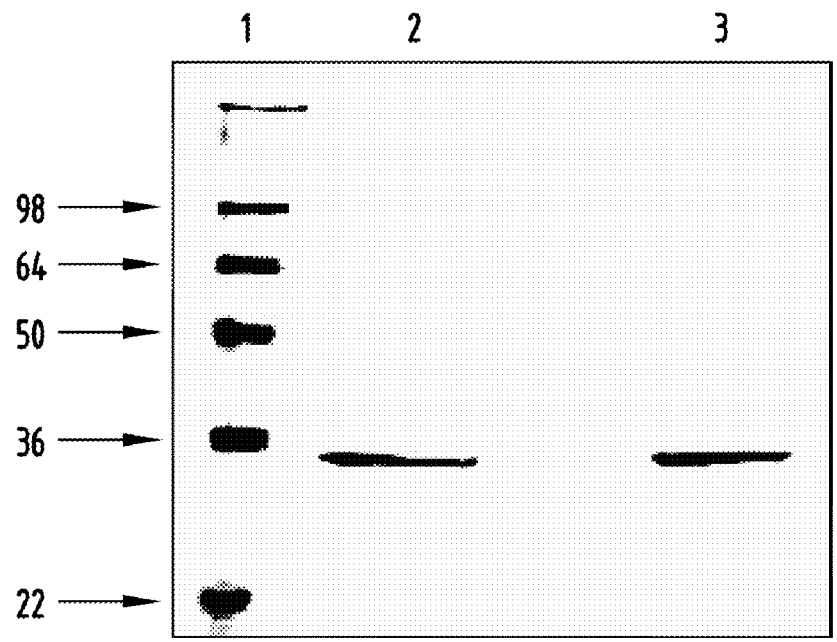
FIG. 1 is a Coomesia staining showing scFv with a single band at 34 kD.

The preferred embodiments of the present invention may be understood more readily by reference to the following detailed description of the specific embodiments and the Examples and Sequence Listing included hereafter.

The text file filed concurrently with this application, titled "VAN67P391.txt" contains material identified as SEQ ID NOS: 1-6, which material is incorporated herein by reference. This text file was created on Jan. 16, 2008, and is 12,288 bytes.

All references, patents, patent publications, articles, and databases, referred to in this application are incorporated-by-reference in their entirety, as if each were specifically and individually incorporated herein by reference.

In accordance with the present invention there may be employed conventional molecular biology, microbiology, and recombinant DNA techniques within the skill of the art. Such techniques are explained fully in the literature, e g, Sambrook et al, "Molecular Cloning A Laboratory Manual" (1989), "Current Protocols in Molecular Biology" Volumes 1-111 [Ausubel, R M, ed (1994)], "Cell Biology A Laboratory Handbook" Volumes 1-111 [J E Cells, ed (1994))], "Current Protocols in Immunology" Volumes 1-111 fCohgan, J E, ed (1994.

DEFINITIONS

The terms used herein have the meanings recognized and known to those of skill in the art, however, for convenience and completeness, particular terms and their meanings are set forth below.

As used in this specification and the appended claims, the singular forms "a", "an", and "the" include plural references unless the context clearly indicates otherwise.

It will be understood by those skilled in the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

The term "antibody" as referred to herein includes whole antibodies and any antigen binding fragment (i.e., "antigen-binding portion") or single chain thereof. The term "antigen-binding fragment" of an antibody, as used herein, refers to one or more fragments of an antibody that retain the ability to specifically bind to an antigen (e.g., Met). It is understood in the art that the antigen-binding function of an antibody can be performed by fragments of a full-length antibody. Examples of antigen-binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody.

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, anchorage dependence, proliferation, malignancy, contact inhibition and density limitation of growth, growth factor or serum dependence, tumor specific markers levels, invasiveness, tumor growth or suppression in suitable animal hosts such as nude mice, and the like, in vitro, in vivo, and ex vivo (see Freshney, Culture of Animal Cells: A Manual of Basic Technique (3rd ed. 1994)).

As used in herein "cell" is used in its usual biological sense, and does not refer to the entire multicellular organism. The cell can exist, for example, in vitro (e.g., in cell culture) or in a multicellular organism, including, e.g., birds, plants and mammals such as humans, cows, sheep, apes, monkeys, swine, dogs, cats, mice and rats. A cell can be prokaryotic (e.g., bacterial cell) or eukaryotic (e.g., an animal or plant cell).

"Nucleic acid" refers to deoxyribonucleotides or ribonucleotides and polymers thereof in either single- or double-stranded form. The term encompasses nucleic acids containing known nucleotide analogues or modified backbone residues or linkages, which are synthetic, naturally occurring, and non-naturally occurring, which have similar binding properties as the reference nucleic acid, and which are metabolized in a manner similar to the reference nucleotides. Examples of such analogues include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses variants thereof (e.g., degenerate codon substitutions that encode the same amino acids) and complementary sequences, as well as the sequence explicitly indicated. The term "nucleic acid" is used interchangeably with gene, cDNA, mRNA, oligonucleotide, and polynucleotide.

The terms "polypeptide", "peptide," and "protein" are used interchangeably herein to refer to a polymer of amino acid residues. The terms apply to amino acid polymers in which one or more amino acid residue is an analogue or mimetic of a corresponding naturally occurring amino acid, as well as to polymers comprising naturally occurring amino acids.

The term "amino acid" includes naturally occurring and synthetic amino acids, as well as amino acid analogues and amino acid mimetics that function in a manner similar to naturally occurring amino acids. Naturally occurring amino acids are those encoded by the genetic code, as well as those amino acids that are later modified, e.g., hydroxyproline, alpha-carboxyglutamate, and O-phosphoserine. Amino acid analogues are compounds that have the same basic chemical structure as a naturally occurring amino acid, i.e., an $\alpha$ carbon that is bound to a hydrogen atom, a carboxyl group, an amino group, and, optionally, an R group (e.g., as in homoserine, norleucine, methionine sulfoxide, methionine methyl sulfonium). Such analogues have modified R groups (e.g., norleucine) or modified peptide backbones, but retain the same basic chemical structure as a naturally occurring amino acid. Amino acid mimetics are chemical compounds that have a structure that is different from the general chemical structure of an amino acid, but that function in a similar manner.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, a conservatively modified variant is a nucleic acid which encodes identical or essentially identical amino acid sequences, or for noncoding nucleic acids, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605 2608 (1985); Rossolini et al., *Mol. Cell. Probes* 8:91 98 (1994)). Because of the degeneracy of the genetic code, a large number of functionally identical nucleic acids encode any given protein. For instance, the codons GCA, GCC, GCG and GCU all encode alanine. Thus, at every position where an alanine is specified by a codon, the codon can be altered to any of the foregoing four codons without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a peptide, polypeptide, or protein sequence which alters, adds or deletes a single amino acid or a small percentage of amino acids in the sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the molecules of the present invention.

The following groups each contain amino acids that are conservative substitutions for one another: 1) Alanine (A), Glycine (G); 2) Serine (S), Threonine (T); 3) Aspartic acid (D), Glutamic acid (E); 4) Asparagine (N), Glutamine (Q); 5) Cysteine (C), Methionine (M); 6) Arginine (R), Lysine (K), Histidine (H); 7) Isoleucine (T), Leucine (L), Valine (V); and 8) Phenylalanine (F), Tyrosine (Y), Tryptophan (W). (see, e.g., Creighton, Proteins (1984)).

A "detectable moiety" or a "detectable label" or an "imaging agent" is an atomic or molecular structure, in the present case, associated with, preferably bound to or conjugated with an Fab or scFv molecule of the present invention that is detectable by any means such as spectroscopic, photochemical, biochemical, immunochemical, or chemical means. For example, useful labels include radionuclides, fluorescent dyes, electron-dense reagents, enzymes (e.g., as commonly used in an ELISA), biotin, digoxigenin, haptens or proteins against which specific antibodies are available.

The terms "mutant," "modified," and "derivative" refer to the manipulation, of nucleic acid sequence or amino acid sequence encoding a protein, by recombinant or synthetic methods, resulting in a change in the nucleic acid sequence or amino acid sequence, respectively, such that the sequence is different from the original or unmanipulated sequence. For example, a nucleic acid sequence or amino acid sequence encoding a protein can be manipulated by extending, shortening, replacing, or otherwise changing the original or unmanipulated sequence, by using the recombinant or synthetic methods described herein or known to one of skill in the art.

The term "imaging" refers to a procedure or modality for generating an image of a detectable label or moiety in vivo, ex vivo, or in vitro, as described herein or known to one of skill in the art. Examples of imaging modalities include magnetic resonance, nuclear magnetic resonance, radioscintigraphy, positron emission tomography, computed tomography, near-infrared fluorescence, X-ray, ultrasound, ultraviolet light, or visible light, but are not limited thereto (for example, see Dahnhert, Radiology Review Manual, 4th Edition, Lippincott, Williams & Wilkins (1999); Brant et al., Fundamentals of Diagnostic Radiobiology, 2nd Edition, Lippincott, Williams & Wilkins (1999); Weissleder et al., Primer of Diagnostic Imaging, 2nd Edition, Mosby-Year Book (1997); Buddinger et al., Medical Magnetic Resonance A Primer, Society of Magnetic Resonance, Inc. (1988); and Weissleder et al., Nature Biotech. 17: 375-378 (1999)).

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e g, bacterial vectors having a bacterial origin of replication and episomal mammalian vectors). Other vectors (e g, non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids In the present specification, "plasmid" and "vector" may be used interchangeably as the plasmid is the most commonly used form of vector. However, the invention is intended to include such other forms of expression vectors, such as viral vectors (e g, replication defective retroviruses, adenoviruses and adeno-associated viruses), which serve equivalent functions.

"Operably linked" when describing the relationship between two polynucleotide sequences, means that they are functionally linked to each other. For example, a promoter is operably linked to a coding sequence if it controls the transcription of the sequence. As a regulatory sequence commonly used promoter elements as well as enhancers may be used. Generally, such expression regulation sequences are derived from genes that are expressed primarily in the tissue or cell type chosen. Preferably, the genes from which these expression regulation sequences are obtained are expressed substantially only in the tissue or cell type chosen, although secondary expression in other tissue and/or cell types is acceptable if expression of the recombinant DNA in the transgene in such tissue or cell type is not detrimental to the transgenic animal By "therapeutically effective dose" or "diagnostically effective dose" herein is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); and Pickar, Dosage Calculations (1999)).

"Subject" or "patient" refers to a mammal, preferably a human, in need of treatment for a condition, disorder or disease.

Antibodies are good delivery tools for targeting Met for treatment or in vivo diagnosis by conjugating chemotherapy compounds, radionuclides, or immunoliposomes for nanoscale delivery, directly fusing the antibody with an immunotoxin or cytokines by recombinant technology (Wu A M, et al. (2005) Nature Biotechnology 23:1137-1146; Mamot C, et al. (2005) Cancer Res 65:11631-11638; Schrama D, et al. (2006) Nature Reviews of Drug Discovery 5: 147-159). The antibody-conjugated drug delivery system directs toxic compounds to and into the targeted malignant tissue or cell specifically, thus decreasing the toxicity of drug to the normal cells and increasing the therapeutic effect by enhancing the accumulated dose of the drug in the targeted tissue.

Conjugation can also increase the solubility of some compounds in a physiological solution, enhance the stability of the compounds, and prevent the conjugated drug from being pumped out of the cells by the multidrug resistance associated p-glycoprotein transmembrane pump (Guillemard V, et al. (2001) Cancer Res 61: 694-699; Guillemard H, et al. (2004) Oncogene 23:3613-3621).

Similar to the therapeutic system, an antibody conjugated to a radionuclide also can provide a new method for the early diagnosis of a malignancy, when a cell surface protein is overexpressed or there is a significant mutated protein on the cell surface.

When using an antibody for drug delivery, internalization of the antibody is usually desired since such internalization allows some compounds to be released from the antibody by liposomes inside of the cells (Schrama D, et al., Nature Reviews of Drug Discovery 5: 147-159). Relatively smaller antibody fragments are preferred because of their relatively high penetrating speed into the solid tumor tissue (Holliger P, et al., (2005) Nature Biotechnology 23: 1126-1136). To avoid the immunogenic effects of xeno antibodies, most antibodies now in clinical use, or in clinical trials, are human antibodies or at least chimeric antibodies comprising a human constant region and a xeno variable region.

In the development and/or practice of the present invention, recombinant antibody phage display technology was applied to mimic many aspects of the process that govern the generation and selection of high affinity natural human antibody in human immune system. An anti-Met phage-display mutated scFv library was built by introducing synthetic diversity within the complementarity-determining regions (CDRs). This library (with a diversity of $9.83 \times 10^8$) was used to select and produce antibodies that bound to human Met antigen with affinity in the 50 nM range. After a total of five rounds of live cells selection and two rounds immobilized recombinant c-Met antigen panning, four unique DNA sequences were found in the higher binding clones. High affinity "scFv-S1" had a dissociation constant value of $5.15 \times 10^{-8}$ mol/L which had been increased 117 times than the original Fab ($K_d=6.04 \times 10^{-6}$ mol/L). scFv-S1 could bind Met on the cell surface specifically, and was analyzed by flow cytometry, immunoprecipitation and immunofluorescent staining. scFv-S1 was transferred into Fab form ("Fab-Met-2"). Fab-Met-2 could bind Met on the cell surface specifically as shown by ELISA and immunoprecipitation analysis. Fab-Met-2 combined with Hum-ZAP complex could be internalized by Met expressed cells and significant cell death occurred only above 100 ng/well of Hum-ZAP and 100 ng human Fab fragments. The inhibition ratios were 73.83% and 62.66% of S114 cells incubated with 800 ng Fab and Hum-ZAP in 72 hrs and 96 hrs.

Thus, the present invention includes novel Met antibody Fab fragment "Met-Fab-2" and scFv fragment "scFv-S1. Met monoclonal antibody fragments Fab-Met-2 and scFv-S1 are produced by the bacterial strains deposited as Patent Deposit Designation PTA-7897 and PTA-7898, respectively, in the American Type Culture Collection. The DNA sequence for the light chain variable region of the anti-Met Fab-Met-2 is identified in the Sequence Listing as SEQ ID NO: 1; the DNA sequence for the heavy chain variable region of the anti-Met Fab-Met-2 is identified in the Sequence Listing as SEQ ID NO: 2; the amino acid sequence of the light chain variable region of the anti-Met Fab-Met-2 is identified in the Sequence Listing as SEQ ID NO: 3; the amino acid sequence of the heavy chain variable region of the anti-Met Fab-Met-2 is identified in the Sequence Listing as SEQ ID NO: 4; the DNA sequence for the anti-Met scFv-S1 is identified in the Sequence Listing as SEQ ID NO: 5; and the amino acid sequence of the anti-Met scFv-S1 is identified in the Sequence Listing as SEQ ID NO: 6. The novel scFv and Fab fragments bind Met in its native state on the cell surface and are internalized. The present novel scFv and Fab fragments have utility for drug delivery and in vivo diagnosis, prognosis, and evaluation of chemotherapeutic response.

The present invention also includes Met-binding antibody fragments that bind to the same epitope (or epitopes) of Met with a binding affinity similar to that of the Fab and scFv fragments produced by the bacteria deposited as ATCC PTA-7897 and PTA-7898, respectively. As used herein, "a binding affinity similar to that of the Fab and scFv fragments produced by the bacteria deposited as ATCC PTA-7897 and PTA-7898, respectively" means fragments having a binding affinity that is at least about 1%, more preferably, at least about 10%, or 20%, or 30%, or 40%, or 50%, or 60%, or 70%, or 80%, or 90%, or 95% of the affinity with which the following binds to Met: Fab or scFv produced by the bacteria deposited as ATCC PTA-7897 or PTA-7898 (respectively), Fab that comprises the amino acids of SEQ ID NO:3 and SEQ ID NO:4 as its V region, or scFv that comprises the amino acids of SEQ ID NO:6. It will be understood by those skilled in the art that the requisite affinity of these other Met-binding antibody fragments is such that the Fab or scFv can be used to carry out the described functions of the molecule, namely, binding to Mets on cells, preferably tumor or cancer cells and internalization by the cells, so that they deliver (a) labeled or detectable agents to the cells for diagnosis and prognosis or (b) drugs for therapy, such as a cytotoxic drug, to kill the cells more effectively than free drug that is not conjugated to the Fab, scFv or derivative.

The novel antibodies and antigen-binding fragments of the present invention are expressed in the bacterial strains deposited as Patent Deposit Designation PTA-7897 and PTA-7898. However, a person of ordinary skill also would understand that these antibodies and fragments can be expressed in various organisms, such as other cells, transgenic plants, animals, fungi, etc. Techniques for the expression of the antibodies and fragments in such organisms are well known in the art.

Binding affinity can be measured by any appropriate antigen-binding assay, e.g., the assay described in Example 6 herein. The affinity of an antibody for an antigen can be determined experimentally using any suitable method (See, for example, Berzofsky et al., "Antibody-Antigen Interactions," In: FUNDAMENTAL IMMUNOLOGY, Paul, W E, Ed, Raven Press New York, N Y (1984), Kuby, J., IMMUNOLOGY, W H Freeman and Co New York, N Y (1992), and methods described herein). The measured affinity of a particular antibody-antigen interaction can vary depending on conditions of measurement (e.g., salt concentration, pH). Thus, measurements of affinity and other antigen-binding parameters (e.g., $K_D$, $IC_{50}$) are preferably made using standardized solutions and buffers such as described herein.

The present invention also includes functional derivatives of the novel Met Fab and scFv fragments described above, which functional derivatives bind to Met with a binding affinity similar to that of the Fab and scFv fragments produced by the bacteria deposited as ATCC PTA-7897 and PTA-7898, respectively. It will be understood by a person of skill in the art that the requisite affinity of the derivative should be such that the functional derivative possesses the same activity and utility as the Fab or scFv molecules discussed above; such as internalization of the Fab or scFv into the cell, and as a carrier for a conjugated drug or label.

Functional derivatives of the anti-Met Fab or scFv fragments described herein include those Fab and scFv fragments that can bind to Met with an affinity that is similar to the affinity with which the anti-Met Fab or scFv described herein binds to Met when measured in any antigen-binding assay, as noted above. Such derivative may be any of (i) a conservatively modified amino acid variant of the H or L chain of said Fab fragment, (ii) a conservatively modified amino acid variant of the scFv fragment, (iii) a deletion variant of said Fab fragment in which part or all of the CH1 or CL domain is deleted, (iv) a deletion variant of said Fab fragment wherein the amino acid sequence of the L chain portion includes at least ten consecutive residues of SEQ ID NO:3 and the H chain portion includes at least ten consecutive residues of SEQ ID NO:4, or (v) a deletion variant of said scFv fragment wherein the amino acid sequence includes at least ten consecutive residues of the L chain portion SEQ ID NO:6 and also includes at least ten consecutive residues of the H chain portion of SEQ ID NO:6.

Fab and scFv derivatives of the present invention may be derived from the provided sequences using techniques well known in the art. The sequence of a functional derivative may differ from the original sequence such that the derivative is has 10% identity with, preferably at least about 20%, 30%, 40%, 50%, 60%, 70%, 80%, 90%, 95%, or 98% identity with: the nucleotide sequence of a Fab including SEQ ID NOs: 1 and 2; the nucleotide sequence of an scFv fragment of SEQ ID NO: 5; the amino acid sequence of a Fab including SEQ ID NOs: 3 and 4; or the amino acid sequence of an scFv fragment of SEQ ID NO: 6.

In accordance with the present invention, a sequence being evaluated (the "Compared Sequence") has a certain "percent identity with," or is a certain "percent identical to" a claimed or described sequence (the "Reference Sequence") after alignment of the two sequences. The "Percent Identity" is determined according to the following formula: Percent Identity=$100[1-(C/R)]$.

In this formula, C is the number of differences between the Reference Sequence and the Compared Sequence over the length of alignment between the two sequences wherein (i) each base in the Reference Sequence that does not have a corresponding aligned base in the Compared Sequence, and (ii) each gap in the Reference Sequence, and (iii) each aligned base in the Reference Sequence that is different from an aligned base in the Compared Sequence constitutes a difference. R is the number of bases of the Reference Sequence over the length of the alignment with the Compared Sequence with any gap created in the Reference Sequence also being counted as a base.

If an alignment exists between the Compared Sequence and the Reference Sequence for which the Percent Identity (calculated as above) is about equal to, or greater than, a specified minimum, the Compared Sequence has that specified minimum Percent Identity even if alignments may exist elsewhere in the sequence that show a lower Percent Identity than that specified.

In a preferred embodiment, the length of aligned sequence for comparison purposes is at least 30%, preferably at least 40%, more preferably at least 50%, even more preferably at least 60%, and even more preferably at least 70%, 80%, 90%, or 95% of the length of the Reference Sequence. The comparison of sequences and determination of percent identity (and percent similarity) between two sequences can be accomplished using any of a number of mathematical algorithms. See, for example, Lesk, A M, ed., Computational Molecular Biology, Lesk, Oxford University Press, New York, 1988; Smith, D W, ed., Biocomputing: Informatics and Genome Projects, Academic Press, New York, 1993; Griffin, A M et al, eds., Computer Analysis of Sequence Data, Part 1, Humana Press, New Jersey, 1994; von Heinje, G., Sequence Analysis in Molecular Biology, Academic Press, 1987; and Gribskov, M et al, eds., Sequence Analysis Primer, Stockton Press, New York, 1991.

A preferred example of such an algorithm is described in Karlin et al. (1993) *Proc. Natl. Acad. Sci. USA* 90, 5873-5877, and is incorporated into the NBLAST and XBLAST programs (version 2.0) as described in Altschul et al. (1997) *Nucleic Acids Res.* 25, 3389-3402. When utilizing BLAST and Gapped BLAST programs, the default parameters of the respective programs (e.g., NBLASST) can be used. In one embodiment, parameters for sequence comparison can be set at score=100, wordlength (W)=I 2, or can be varied (e.g., W=5 or W=20).

In a preferred embodiment, the percent identity between two nucleotide sequences is determined using the GAP program in the GCG software package (Devereux et al. (1984) *Nucleic Acids Res.* 12 (1):387) using a NWSgapdna. CMP matrix and a gap weight of 40, 50, 60, 70, or 80 and a length weight of 1, 2, 3, 4, 5 or 6.

Another algorithm utilized for the comparison of sequences is that of Myers and Miller, CABIOS (1989), and is incorporated into the ALIGN program (version 2.0; part of the CGC software package (supra). Additional known algorithms for sequence analysis include ADVANCE and ADAM (Torellis et al. (1994) *Comput. Appl. Biosci.* 10, 3-5); and FASTA Pearson et al. (1988) *Proc. Nat'l. Acad. Sci* 85, 2444-2448).

Amino acid substitutions, deletions, or additions, can be made in either the FRs or in the CDRs. While changes in the framework regions are usually designed to improve stability and reduce immunogenicity of the antibody, changes in the CDRs are usually designed to increase affinity of the antibody for its target. Such affinity-increasing changes are typically determined empirically by altering the CDR region and testing the antibody, as describe herein Alterations can be made according to the methods described in Antibody Engineering, 2nd ed (1995), ed Borrebaeck, Oxford University Press. An exemplary method for making a VH domain that is an amino acid sequence variant of the VH domain of the Fab described herein, comprises a step of adding, deleting, substituting or inserting one or more amino acids in the VH, optionally combining the VH domain with one or more VL domains, and testing the VH domain or VH/VL combination or combinations for specific binding to Met, and/or internalization into Met-expressing cells, and (preferably) testing the ability of such antigen-binding domain to modulate one or more Met-associated activities. A similar approach would be used to create and test variants of the VL domain disclosed herein, whether used alone or combined with one or more VH domains.

In one embodiment such functional derivative is a deletion variant of the Fab or scFv fragments in which all or part of (a) the CH1 or the CL domain of the Fab is deleted, (b) the linker peptide of the scFv is deleted, or (c) the L chain includes at least 10 contiguous residues of SEQ ID NO:3 and H chain includes at least 10 contiguous residues of SEQ ID NO:4.

Further, a functional derivative of the Fab or scFv fragments may have CDR sequences that differ insubstantially from those of the Fab or scFv fragments described herein. Insubstantial differences include minor amino acid changes, such as 1 or 2 substitutions out of any of 5-7 amino acids in the sequence of a CDR. An amino acid can be substituted by an amino acid having similar charge, hydrophobic, or stereochemical characteristics. Such substitutions would be within the skills of a person of ordinary skill in the art. More substantial changes could be made in structure framework regions (FRs) without adversely affecting the binding properties of the Fab or scFv fragment.

The antibody or antigen-binding fragment of the present invention may comprise an immunogenic peptide having at least 200, 100, 90, 80, 70, 60, 50, 40, 30, 20, or 10 consecutive residues of SEQ ID Nos. 3, 4, or 6. Further, the antibody or fragment is an immunogenic peptide comprised of 5-20, 10-40, 20-75, or 50-100 contiguous amino acid residues of SEQ ID Nos. 3, 4, or 6. In one embodiment, the antibody or fragment can bind to Met with an affinity that is similar to the affinity with which the anti-Met Fab or scFv described herein binds to Met when measured in an antigen-binding assay.

In another embodiment of the present invention, the Fab or scFv fragment, or derivative thereof, is coupled or conjugated to a detectable label or an imaging agent. There are many different detectable labels and methods of labeling known to those of ordinary skill in the art. Examples of the types of labels which can be used in the present invention include radioactive isotopes, paramagnetic isotopes, and compounds which can be imaged by positron emission tomography (PET). Those of ordinary skill in the art will know of other suitable labels for binding to the antibodies used in the invention, or will be able to ascertain such, by routine experimentation. Diagnostically-labeled (e.g., radiolabeled) antibodies are effective.

Suitable detectable labels for diagnosis and imaging include radioactive, fluorescent, fluorogenic, chromogenic, or other chemical labels. Useful radiolabels, which are detected simply by gamma counter, scintillation counter, PET scanning or autoradiography include 3H, 124I, 125I, 131I, 35S and 14C. In addition, 131I is a useful therapeutic isotope (see below).

Common fluorescent labels include fluorescein, rhodamine, dansyl, phycoerythrin, phycocyanin, allophycocyanin, o-phthaldehyde and fluorescamine. The fluorophore, such as the dansyl group, must be excited by light of a particular wavelength to fluoresce. See, for example, Haugland, Handbook of Fluorescent Probes and Research Chemicals, Sixth Ed., Molecular Probes, Eugene, Oreg., 1996). Fluorescein, fluorescein derivatives and fluorescein-like molecules such as Oregon Green and its derivatives, Rhodamine Green and Rhodol Green, are coupled to amine groups using the isothiocyanate, succinimidyl ester or dichlorotriazinyl-reactive groups. Similarly, fluorophores may also be coupled to thiols using maleimide, iodoacetamide, and aziridine-reactive groups. The long wavelength rhodamines, which are basically Rhodamine Green. derivatives with substituents on the nitrogens, are among the most photostable fluorescent labeling reagents known. Their spectra are not affected by changes in pH between 4 and 10, an important advantage over the fluoresceins for many biological applications. This group includes the tetramethylrhodamines, X-rhodamines and Texas Red. derivatives. Other preferred fluorophores for derivatizing the peptide according to this invention are those which are excited by ultraviolet light. Examples include cascade blue, coumarin derivatives, naphthalenes (of which dansyl chloride is a member), pyrenes and pyridyloxazole derivatives. Also included as labels are two related inorganic materials that have recently been described: semiconductor nanocrystals, comprising, for example, cadmium sulfate (Bruchez, M. et al., Science 281:2013-2016 (1998), and quantum dots, e.g., zinc-sulfide-capped cadmium selenide (Chan, W., et al., Science 281:2016-2018 (1998)).

In yet another approach, the amino groups of the Fab fragment or derivative thereof are allowed to react with a reagent that yields a fluorescent product, for example, fluorescamine, dialdehydes such as o-phthaldialdehyde, naphthalene-2,3-dicarboxylate and anthracene-2,3-dicarboxylate. 7-nitrobenz-2-oxa-1,3-diazole (NBD) derivatives, both chloride and fluoride, are useful to modify amines to yield fluorescent products.

The Fab and scFv fragments, and functional derivatives thereof, can also be labeled for detection using fluorescence-emitting metals such as $^{152}$Eu+, or others of the lanthanide series. These metals can be attached to the peptide using such metal chelating groups as diethylenetriaminepentaacetic acid (DTPA) or ethylenediamine-tetraacetic acid (EDTA). DTPA in anhydride form can readily modify the NH2-containing antibodies.

For in vivo diagnosis, radionuclides may be bound to the antibody either directly or indirectly using a chelating agent such as DTPA and EDTA. Examples of such radionuclides are $^{99}$Tc, $^{123}$I, $^{125}$I, $^{131}$I, $^{111}$In, $^{97}$Ru, $^{67}$Cu, $^{67}$Ga, $^{68}$Ga, 72As, $^{89}$Zr, $^{90}$Y and $^{201}$Tl.

Generally, the amount of labeled antibody needed for detectability in diagnostic use will vary depending on considerations such as age, condition, sex, and extent of disease in the patient, contraindications, if any, and other variables, and is to be adjusted by the individual physician or diagnostician. Dosage can vary from 0.01 mg/kg to 100 mg/kg.

The Fab and scFv fragments, and functional derivatives thereof, can also be made detectable by coupling or conjugating them to a phosphorescent or a chemiluminescent compound. The presence of the chemiluminescent-tagged peptide is then determined by detecting the presence of luminescence that arises during the course of a chemical reaction. Examples of particularly useful chemiluminescers are luminol, isoluminol, theromatic acridinium ester, imidazole, acridinium salt and oxalate ester. Likewise, a bioluminescent compound may be used to label the peptides. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In yet another embodiment, colorimetric detection is used, based on chromogenic compounds which have, or result in, chromophores with high extinction coefficients.

In situ detection of the labeled Fab or scFv fragment, or functional derivative thereof, may be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

For diagnostic in vivo radioimaging, the type of detection instrument available is a major factor in selecting a radionuclide. The radionuclide chosen must have a type of decay, which is detectable by a particular instrument. In general, any conventional method for visualizing diagnostic imaging can be utilized in accordance with this invention. Another factor in selecting a radionuclide for in vivo diagnosis is that its half-life be long enough so that the label is still detectable at the time of maximum uptake by the target tissue, but short enough so that deleterious irradiation of the host is minimized. In one preferred embodiment, a radionuclide used for in vivo imaging does not emit particles, but produces a large number of photons in a 140-200 keV range, which may be readily detected by conventional gamma cameras.

A preferred diagnostic method is radioimmunoscintigraphic analysis, which is preferably performed in a manner that results in serial total body gamma camera images and allows determination of regional activity by quantitative "region-of-interest" (ROI) analysis.

The diagnostically labeled Fabs, scFvs, and functional derivatives thereof may be incorporated into convenient dosage forms. Preferably, for diagnosis, the labeled antibodies are administered systemically, e.g., by injection or infusion. When used, injection or infusion may be by any known route, preferably intravenous injection or infusion, subcutaneous injection, intramuscular, intracranial or intrathecal injection or infusion, or intraperitoneal administration. Injectables can be prepared in conventional forms, either as solutions or suspensions, solid forms.

Radioimmunoscintigraphy is an important and attractive modality for experimental and clinical molecular imaging of cancer. Established methods for radiolabeling antibodies in suitable quantity and of appropriate quantity for scintigraphy are available, feasible, relatively inexpensive, and adaptable to virtually any antibody regardless of its epitopic specificity. New radiolabeling methods are continually emerging, and many laboratories are evaluating a wide range of antibody derivatives—from full-length chimeric and humanized molecules, to monomeric and multimeric antibody fragments, to immunoconjugates—as potentially superior imaging and therapeutic agents, with improved targeting selectivity and more favorable biological turnover kinetics (Program and Abstracts, Ninth Conference on Cancer Therapy with Antibodies and Immunoconjugates. 2002. Cancer Biotherapy & Radiopharmaceuticals 17:465-494).

Moreover, the reagents, supplies, and equipment required to perform radioimmunoscintigraphy in experimental animals and in humans are commonplace. For decades decommissioned or refurbished clinical gamma cameras have proven satisfactory for animal imaging applications, and they continue to do so. Modified or custom-built gamma cameras adapted for small animal imaging are becoming more widely available.

The major advantage of scintigraphy as a molecular imaging modality (not limited to imaging with antibodies) is that the acquired images are inherently quantitative. The physics of gamma radiation and the mathematical analysis of nuclear images, including corrections for photon attenuation and other artifacts, are well understood. In animal models as well as in human studies one can noninvasively and accurately measure net accumulation and some kinetic parameters of radiopharmaceutical interactions with target lesions, and the concurrent collection of even a small set of biological samples (e.g., blood and excreta) for direct counting combined with quantitative analysis of diagnostic images enables useful dosimetry estimates for therapeutic purposes.

Many different radiopharmaceuticals are available for imaging neoplasms. They range from classical agents such as sodium iodide (Na—$^{131}$I), thallium chloride ($^{201}$TlCl), and gallium citrate ($^{67}$Ga-citrate) to highly selective positron-emitting reporter gene detection systems (Vallabhajosula, S (2001), In: Nuclear Oncology. I Khalkhali et al., eds. Lippincott Williams & Wilkins, Philadelphia, Pa. pp. 31-62; Iyer M et al. (2001) *J Nucl Med* 42, 96-105). Radiolabeled molecules that bind to specific cell surface components provide one successful approach to tumor imaging and therapy. Examples are OCTREOSCAN® for imaging and potentially treating neuroendocrine neoplasms, CEASCAN® and ONCOSCINT® for imaging colorectal and ovarian cancers, and BEXXAR® and ZEVALIN® for detecting and treating certain lymphomas.

In another embodiment of the present invention, the Fab, scFv fragment, or functional derivative thereof is coupled or conjugated to a drug. For example, the Fab or scFv fragment or functional derivative is conjugated to a chemotherapeutic drug. Therapeutic compositions or methods for treating tumors and cancer may comprise one (or more) anti-tumor drugs or agents, such as mitotic inhibitors (e.g., vinblastine); alkylating agents (e.g., cyclophosphamide); folate inhibitors (e.g., methotrexate); antimetabolites (e.g., 5-fluorouracil and cytosine arabinoside); intercalating antibiotics (e.g., adriamycin and bleomycin); promoters of microtubule polymerization (e.g., paclitaxil) or enzyme inhibitors (e.g., topoisomerase inhibitors, such as etoposide).

Another embodiment, the present invention is a pharmaceutical or a diagnostic composition of the present Fab or scFv fragment or a functional derivative thereof. In said composition the Fab or scFv, or derivative thereof, is dissolved in a pharmaceutically acceptable carrier, preferably an aqueous carrier. A variety of aqueous carriers can be used, e.g., buffered saline and the like. These solutions are preferably sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies, Fab fragments, or scFv fragments when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical compositions comprising a known cancer therapeutic in combination with the conjugates disclosed herein are within the scope of this invention. The pharmaceutical composition may also comprise one or more other medicaments to treat additional symptoms for which the target patients are at risk, for example, anti-infectives including antibacterial, anti-fungal, anti-parasitic, anti-viral, and anti-coccidial agents, since tumor-bearing patients may also suffer from various infections or have diminished resistance to infections.

Also within the scope described herein are kits comprising the pharmaceutical or diagnostic composition of the present Fab, scFv fragment, or functional derivatives thereof. The kit can further contain a least one additional reagent.

The present invention also includes a method for diagnosing a Met-expressing tumor or cancer in a subject. In this method, the present Fab or scFv fragment, or a functional derivative thereof, is conjugated to an imaging agent or detectable label is administered to a subject suspected of having a Met-expressing tumor or cancer. Detection of the imaging agent in or on cells or in a tissue is diagnostic of said tumor or cancer.

Another method of the present invention is detecting the presence of abnormal cells or tissues in a subject in which the amount or level of Met expression is abnormally high compared to a known control amount or level of Met in normal cells or tissues. This method includes: (a) administering to the subject the present anti-Met Fab or scFv fragment, or derivative thereof; (b) measuring the binding of said fragment to cells or tissue of the subject by measuring the amount or level of the label or imaging agent to determine the Met amount or level and (c) comparing the amount or level of Met measured in step (b) to said known control amount or level. In this method, a higher amount or level measured in step (b) compared to said normal amount or level is indicative of the presence of said abnormal cells or tissues in the subject. Further, an imaging agent, as described above, can be conjugated to the Fab, scFv fragment, or derivative. In one embodiment, the abnormal cells are tumor or cancer cells or the abnormal tissue is tumor or cancer tissue.

Additionally, another use of the anti-Met Fab fragment or scFv fragment, or derivative thereof, is in a method for enhancing the response of a subject with a Met-expressing tumor or cancer to a chemotherapeutic drug directed to said tumor or cancer. In this method, the Fab or scFv fragment or derivative thereof is administered to the subject an effective amount, and is (i) is internalized by cells of the tumor or cancer, and (ii) conjugated to said chemotherapeutic drug such that the binding of the drug-conjugated Fab or scFv fragment, or derivative thereof, to the tumor or cancer cells results in internalization of the drug-conjugated fragment or derivative, and leads to enhanced response of the subject to the drug as compared to administration of the drug alone.

Having now generally described the invention, the same will be more readily understood through reference to the following examples, which are provided by way of illustration, and are not intended to be limiting of the present invention, unless specified.

EXAMPLES

Example 1

Materials and Methods for Examples 2-8

Cell Lines

NIH 3T3, S114 (NIH 3T3 cells stably transfected with the human HGF/SF receptor c-Met genes). MKN45 (human gastric carcinoma cell line) cells were cultured in RPMI supplemented with 10% FBS. All cell lines were maintained at 37° C. under an atmosphere of 5% CO2.

Diversity Design for CDRs of VH and VL

The primers were used for VL sub-library construction: Vk1, 5'-GGG CCC AGG CGG CCG AGC TCC AGA TGA CCC AGT CTC C-3'; Vk2, 5'-GAAA GCC CCT AAG CTC CTG ATC TAT NNS NNS NNS AGT TTG CAA AGT GGG GT CCC ATC AAG-3'; Vk3, 5'-TCG TTT GAT CTC CAG CTT GGT CCC CTG GCC AAA AGT WNN WNN WNN WNN WNN WNN CTG TTG ACA GTA GTA AGT TGC AAA ATC-3'; Vk4, 5' GGA AGA TCT AGA GGA ACC TTT GAT CTC CAG CTT GGT CCC CTG 3'. The primers were used in VH sub-library construction: VH1, 5' GGT GGT TCC TCT AGA TCT TCC TCC TCT GGT GGC GGT GGC TCG GGC GGT GOT GGG GAG GTG CAG CTG GTG GAG TCT GG 3'; VH2, 5'-GCA GCC TCT GGA TTC ACC TTC AVT RVM WMY KMT ATG CAC TGG GTC CGC CAG GCT-3'; VH3, 5'-CCA GGC AAG GGG CTG GAG TGG GTG GCA DHT NNS DGG DMT DMT GGA AGT AHC AVV TAC TAT GCA GAC TCC GTG AAG GGC CG-3'; VH4, 5'-CG GCC CTT CAC GGA GTC TGC ATA GTA BBT GDT ACT TCC AKH AKH CCH WNN ADH TGC CAC CCA CTC CAG CCC CTT GCC TGG-3'; VH5, 5'-CGA TGG GCC CTT GGT GGA GGC AGG GGA GAC GGT GAC CAG GGT GCC CTG GCC CCA GTA GTC AAA WNN WNN WNN WNN WNN KYK CGC ACA GTA ATA CAC AGC CGT-3'; VH6, 5'C CTG GCC GGC CTG GCC ACT AGT GAC CGA TGG GCC CTT GGT GGA GGC AGG GGA GAC GGT GAC CAG GGT GCC 3'. DNA degeneracies were represented using the IUB code and represent equimolar mixtures: N=A/C/G/T, D=A/G/T, V=A/C/G, B=C/G/T, H=A/C/T, K=G/T, M=A/C, R=A/G, S=G/C, W=A/T, Y=C/T.

For VH sub-library construction, the first PCR was carried out using Taq DNA polymerase (invitrogen) in a 50 µl volume. The PCR program consisted of 4 min at 94° C.; 50 sec at 94° C., 50 sec at 45° C., 1 min at 72° C. for 30 cycles then 10 min at 72° C. The primers VH2/VH6 and VH1/VH5V were added for CDRH1, CDRH3 mutation respectively, and VH2/VH5 for CDRH1 and CDRH3 mutation simultaneously. A second PCR for the whole VH construction including CDR-H1 and CDR-H3 consist of the primers VH1/VH6 and the DNA templates of first PCR products. The PCR program consisted of 4 min at 94° C.; 50 s at 94° C., 50 s at 50° C., and 1 min at 72° C. for 30 cycles and then 10 min at 72° C. A third PCR was then carried out using Taq DNA polymerase, 4 µl of each of the "second PCR", 25 pmol of each of the oligonucleotides VH1/VH4 and VH3/VH6 (including CDRH2 sequence) in a 100 µl reaction volume. The PCR program consisted of 4 min at 94° C.; 50 s at 94° C., 50 s at 50° C., and 1 min at 72° C. for 30 cycles and then 10 min at 72° C.

For VL sub-library construction, the first PCR ("intermediate" PCRs) program consisted of 4 min at 94° C.; 50 sec at 94° C., 50 sec at 45° C., 1 min at 72° C. for 30 cycles then 10 min at 72° C. VK1/VK3 and VK2/VK4 were used for CDRL2, CDRL3 mutation respectively. A second PCR ("assembly PCR") was then carried out using Taq DNA polymerase, 2 µl of each of the "intermediate" PCR, 25 pmol of each of the oligonucleotides VK1 and VK4 in a 100 µl reaction volume. The assembly PCR program consisted of 4 min at 94° C.; 50 s at 94° C., 50 s at 50° C., and 1 min at 72° C. for 30 cycles and then 10 min at 72° C.

Construction of scFv Library

For scFv gene assembling, VH and VK genes are mixed in equal ratios to generate the overlap product. The primers in the first-round PCR create complementary sequences in the downstream region of the light-chain variable regions and the upstream region of the heavy-chain variable regions that serve as the overlap for the extension of the full-length product. The purified scFv gene was digested with the restriction enzyme SfiI (Roche Molecular Biochemicals, Mannheim, Germany), and ligated into the phagemid pComb3XSS (Kindly provided by the Barbas laboratory, the Scripps Research Institute, La Jolla, Calif.). After the ligation, recombinant phagemids were ethanol-precipitated and electrotransformed into *Escherichia coli* XL1-Blue (Stratagene, La Jolla, Calif.).

Selection of Met-Binding Phage on Cell Lines

S114 cells growing on a 75 cm$^2$ cell culture flask (90% confluence) were removed in 10 ml cell dissociation buffer (enzyme free, PBS based) and washed twice in cold PBS (30 ml). To deplete the library of non-specific phage, 5×10$^6$ NIH 3T3 cells were incubated with 50 ul of phage antibody library in 1 ml complete media (DMEM-10% FCS) for 0.5 h rocking at 37° C. NIH 3T3 cells were pelleted by centrifugation at 2500 rpm and the supernatant was removed. S114 cells were incubated in a 15 ml tube with depleted phage antibody library (supernatant from the previous step) for 1 h at RT. Cells were subsequently washed with washed 10 times in cold complete media. Cells were incubated for 30 min at 37° C. in 3 ml pre-warmed completed media to allow receptor internalization. Non-internalized phage were removed from cell surface by washing in cold glycine buffer (50 mM glycine, 150 mM NaCl, 200 mM urea, pH2.2) 2 times and then 10 washes in cold complete media and a final wash in cold PBS. Cells were sonicated 5 min in trypsin-EDTA and incubated in 37° C. for 10 min.

Selection of Met-Binding Phage on Immobilized Met Antigens

Phage library were incubated with 3% BSA for 30 min at RT and transferred into Met coated immunoplates 1 h at 37° C. Unbound phages were washed off with PBS/0.2% Tween-20 for 10-20 times. Antigen-bound phages were eluted off using 0.5 ml trypsin-EDTA. The eluted phages were used to infect exponentially growing (OD$_{600}$ of 0.5) XL1-Blue for 30 min at 37° C. Phage were amplified and pelleted for the next round pannin. After five rounds of cell panning and two rounds immobilized antigen selection, random monoclonal phage were selected and screened by phage ELISA.

Phage Rescue and Amplification

Phage was titered by infection of eluted phage into XL1-Blue, and prepared for the next round of selection rescued with helper phage VCSM13. After overnight growth at 30° C., phage were purified and concentrated from bacterial supernatant with polyethylene glycol 8000 (PEG8000), and re-suspended in 1 ml 1% BSA-PBS for use in the next round panning.

Monoclonal Phage ELISA

Inoculate individual colonies from the titration plates from the final round of selection into 100 µl SB containing 100 µg/ml ampicillin and 1% glucose in 96 cell-well plate, grow shaking overnight at 37° C. Transfer 2 µl from each well of this plate to a second 96 cell-well plate containing 200 µl of SB with 100 µg/ml ampicillin and 1% glucose per well. Growing shaking at 37° C. for 2 h, add 25 µl 2xYT containing 100 µg/ml ampicillin, 1% glucose and 10$^9$ helper phage. Shake for 1 h and aspirate off the supernatant, resuspend pellet in 200 µL 2xYT containing 100 µg/ml ampicillin and 20 µg/ml kanamycin, growing shaking overnight at 30° C. Spin the plate and add the supernatant 100 µl to the 96 well plate which coated with Met and blocked with BSA. After incubate for 1 h, washing 3 times with PBS-0.2% Tween-20. Add 1:5000 dilution of HRP-anti-M13 in 3% PBS for 1 h, add 100 ug/ml TMB to each well, and leave at room temperature for 10 min, stop the reaction by adding 50 µl 1M sulfuric acid, read the OD at 450 nm.

scFv Expression and Purification

To express a large amount of scFv, scFv gene was cloned into pBAD/gIII vector and transformed into *E. coli* TOP10 F' cells. Exponentially growing *E. coli* TOP10 F' cells were were plated on LB plates containing 100 mg/ml ampicillin, followed by incubation at 37° C. overnight. Single ampicillin-resistant clone was picked and grown in 2 ml SB medium containing 100 mg/ml ampicillin, cultured at 37° C. overnight with shaking. Diluted with 100 ml of fresh medium for further incubation for 2 h at 37° C. with shaking, and induced with 0.02% L-arabinose for expression of scFv to form inclusion body at 37° C. overnight. Inclusion bodies were re-suspended in 6M Guanidine-HCl/Tris-NaCl (PH8.0) buffer, and rocking at 4° C. overnight to dissolve the protein completely. The guanidine was gradually removed by dialyzing against decreasing concentration of Gu-HCl in Tis-HCl/NaCl buffer at 4° C. The concentration of Gu-HCL in the dialysis buffer was lowered sequentially (3, 2, 1, 0.5 and 0 M). 375 uM oxidizing reagent-glutathione and 0.4 M of L-arginine were included in the 1- and 0.5-M Gu-HCl/Tris dialysis buffers. scFv was purified by immotal metal-affinity chromatography (IMAC).

SDS-PAGE and Western Blot Analysis

Protein samples were analyzed by electrophoresis on 10% SDS-PAGE under reducing condition. The gel was stained with Coomassie blue. For Western blots, proteins were electrophoretically transferred onto nitrocellulose membranes. The membranes were first blocked by incubation with 5% nonfat milk and then incubated with mouse anti-Myc antibody, further incubated with goat antimouse/horseradish peroxidase conjugate antibody followed by washing steps, and finally developed using the ECL detection system and exposed to X-ray film.

Immunoprecipitation

Cells (S114, MKN45 and NIH 3T3) were grown in 150-cm$^2$ flasks to near-confluency before lysed. 20 μg of scFv/20 μg anti-myc Ab and 100 μl of protein-G-Sepharose beads (Invitrogen, USA) were added to 1.0 ml of cell lysates (with 0.5 mg of total protein) and incubated at 4° C. overnight with gentle shaking. The immune complexes were washed twice, and the proteins were denatured with 2×SDS sample buffer by boiling at 100° C. for 5 min. The protein samples were separated by 4-15% SDS-PAGE and transferred onto nitrocellulose membrane (Bio-Rad, USA). The membrane was blocked with milk blocking buffer at RT for 1 hr, and was incubated with rabbit anti-human Met polyclonal antibody C-28 (Santa Cruz Biotechnology, USA) at 1:200 dilution for 1.5 hr at RT, washed four times in wash buffer, and reacted with donkey anti-rabbit IgG-HRP conjugate (Amersham, USA) at 1:5,000 dilution for an additional 1.5 hr at RT. Following the same washing, the proteins were detected by a chemiluminescence assay as recommended by the manufacturer (Pierce, USA).

FACS Analysis

S114 and NIH 3T3 cells (1.0×10$^6$) were blocked with BSA blocking buffer for 15 min at 4° C. After washing twice with PBS, the cells were incubated with scFv to a final concentration of 0.2 mg/ml and mouse anti-Myc antibody at 4° C. for 30 min. After washing with PBS, the cells were stained with goat anti-mouse IgG FITC conjugate (Sigma-Aldrich, USA) at 1:10 dilution at 4° C. for 30 min. The cells were then washed twice and suspended in 500 μl PBS. Flow cytometry was performed with a FACS Calibur cytometer and the CellQuest analysis program (Becton Dickinson, Heidelberg, Germany).

Cell Binding and Internalization of Phage Antibody and scFv

Conformation of anti-Met phage antibody internalization was obtained by confocal microscopy. S114 cells were grown in slide chambers and at 80% confluence, and incubated with phage antibody (10$^{12}$ cfu/ml, in fresh complete media) for 0.5, 1 and 2 h at 37° C. Chambers were placed on ice to halt receptor internalization and chambers were washed 10 times in cold PBS, and 10 min in cold glycine buffer, pH2.8 (50 mM glycine, 150 mM NaCl) to remove surface bound antibody. Cells were washed two twice in cold PBS, fixed in 4% paraformaldehyde for 10 min at room temperature and then permeabilized in cold methanol for ten min at room temperature. Chamber was incubated with anti-M13 antibody (1:2000) for 1 h followed by three washes with complete media. Phages were detected by incubation with FITC-anti-mouse antibody (1:50) for 1 h while followed by three washes in complete media. Images were collected using a Leica TCS NTconfocol laser fluorescence microscope.

For co-localization detection, MKN45 and NIH 3T3 cells were grown in the same chamber at 60% confluence, washed twice in PBS (1 ml/per well). Cells were fixed with 50% acetone and 50% methanol for 5 min at RT. Blocked the cells in 3% BSA, 30 min at RT. Cells were incubated with scFv/anti-Myc Ab and rabbit anti-Met (c-28) Ab for 1 h at 37° C., followed by three washes with PBS. Add Rhodamine-red conjugated anti-mouse antibody (1:150) and FITC-conjugated anti-rabbit antibody (1:50) in chambers, 200 ul for each well. Incubate the chamber for 1 h at 37° C. Cells were washed three twice with PBS. Stained the nucleus with DAPI for 5 min at RT and follows two washes with PBS. Images were collected using a Leica TCS NT confocal laser fluorescence microscope.

Construction of Fab from scFv and Fab Expression

VH and VL genes of scFv were amplified and connected with CH and CL amplified from pCom3XTT (provided by Barbas, Scripps Institute) by overlap PCR, and Fab gene was assembled with Fd and L, and digested with SfiI, cloned into pComb3XSS phagemid. Transformed the recombinant plasmid into E. coli TOP10 and culture the plate containing 100 μg/ml ampicillin and 1% glucose. Expression of soluble Fab fragment was induced on 1000-ml scale in SB medium containing 100 μg/ml and 1 mM IPTG at 25° C. for 16 h. Fab fragment were purified on an ImmunoPure Immobilized Protein-L column (Piece) from the medium and periplasmic extracts using a FPLC system (Amersham Pharmacia Biotech, Uppsala, Sweden)

Affinity Measurement

Non-competitive enzyme-linked immunosorbent assay has been widely used for the measurement of antibody affinity constant which describes the binding degree of antibody-antigen interaction. According to David Beatty's method to the measurement of antibody-antigen affinity based on the Law of Mass Action, a mathematical equations have been developed to calculate the affinity constant. The most commonly used formula was established by David Beatty and the equation was $K_{aff}=(n-1)/(2\{n[Ab']_t-[Ab]_t\})$ ($n=[Ag]/[Ag']$). This method utilized OD-50 of the sigmoid curve and obviated the need for affinity purification of antibody used as standard. Using serial dilutions of both antigen ([Ag], [Ag']) and antibody (scFv antibody), the affinity constant ($K_{aff}$) was measured by non-competitive ELISA. Two sigmoid curves of optical density (OD) versus logarithms of antibody concentrations were estimated by SPSS 10.0 software. The maximum value of OD (OD-100) of each curve was computed respectively and OD-50, half of OD-100, was obtained. Then the concentrations of antibody corresponding to OD-50 on the curves, named $[Ab]_t$ and $[Ab']_t$ were calculated. For $[Ag']=\frac{1}{2}[Ag]$, $K_{aff}=1/\{2[Ab']_t-[Ab]_t\}$.

Cytotoxicity Assay of Fab Combined with Saporin Conjugated Anti-Human IgG

S114 cells were plated in 96-well plates at 2000 cells/100 μl/well. The plates were incubated 16 hours at 37° C. in the presence of 5% CO2. Anti-Met Fab and Hum-ZAP were diluted in DMEM medium and added to the wells in different concentration. The plates were incubated 72 and 96 hours at 37 C in the presence of 5% CO2. After 3-4 days culture, cell proliferations were measured with MTS/PMS. For each plate, 75 μl (phenazine methosulfate) PMS (0.92 mg/ml in Dulbecco's PBS) were added to 1.5 ml (3-(4,5-dimethylthiazol-2yl)-5-(3-carboxymethoxyphenyl)-2-(4-sulfophenyl)-2H-tetrazolium, inner salt) MTS (2 mg/ml in Dulbecco's PBS), and 20 ul were added to each well. The plates were incubated 1-3 hours at 37 C in the presence 5% CO2. Read the absorbance value at 492 nm in Spectra (KC4, BIO-TEK Instruments, Inc.). The curves were generated using the percent of the control's surviving cells, the concentration of primary antibody at which the antibody and Hum-ZAP complete eliminated fifty percent of the cells (ED50) is calculated from that curve.

Example 2

Library Construction

CDR-L1 was held constant, and CDR-L2 and CDR-L3 were randomized. Positions chosen for randomization in CDR-L2 and CDR-L3 are 50, 51 and 52 in CDR-L2, and 92, 93, 94, 95 and 96 in CDR-L3 with random codon NNS. VL sub-library was assembled sequentially using polymerase chain reaction (PCR) by overlap extension. A set of position within CDR-H1 and CDR-H2 were chosen for mutation. Positions 30-33in CDR-H1, and 51, 52, 53, 54, 57 and 58 in CDR-H2 were mutated. Tailored degenerate codons AVA RVM WMY KMT were used for CDR-H1; and NNS DGG DMT DMT GGA AGT AHC AVV for CDR-H2. DHT was chosen for Fr2 50 (GTT) in the VH mutation library. At the N-terminal boundary of CDRH3, Ala97-Arg98 were changed to Ala-Arg/Lys which was found most commonly amongst human antibodies in the Kabat database. For 99-102 aa, NNS codon was used for random mutation. The scFv genes were assembled by overlap PCR with different VH and VL libraries gene fragments. After several transformations, a scFv phage antibody library containing $9.83 \times 10^8$ members was established.

VH and VL mutants were used for construction of the variable libraries and for high affinity antibody selection. CDR3s are important to antibody affinity maturation and CDR-L3 randomization could improve light chain diversity. CDR-L2 which only contains 3 amino acids has also been randomized. For the generation of heavy chain libraries in the scFv format, a set of positions within CDR-H1 and CDR-H2 was chosen for limited mutation or randomization. Positions 31-34 in CDR-H1, and 51-54, 57 and 58 in CDR-H2 were mutated.

CDR-H3 is located at the center of the antigen-binding site, and it is the most variable amongst the six CDRs in natural antibodies, both in terms of amino acid composition, length, and conformation. As a result, CDR-H3 is often the most important determinant for the specificity of antibodies. In the Kabat database, the C-terminal boundaries of natural CDR-H3 sequences are not highly variable, but rather, usually contain either Phe-Asp-Tyr or Ala-Met-Asp-Tyr immediately preceding position 102. As the anti-Met CDR-H3 contains a Phe-Asp-Tyr motif at its C-terminal boundary, this region was left constant. At the N-terminal boundary of CDRH3, the framework was changed slightly from that of the anti-Met Fab sequence (Ala97-Arg98) to the sequence found most commonly amongst human antibodies in the Kabat database (Ala-Arg/Lys) (Hoogenboom, G. R. (1997) *Trends Biotechnol.* 15: 62-70; Zemlin, M., et al. (2003) *J. Mol. Biol.* 334, 733-749; Rothlisberger, D., et al., (2005) *J Mol Biol,* 347, 773-789; Lee, C., et al. (2004) *J. Mol. Biol.* 340, 1073-1093).

Example 3

Subtractive Cellular and Immobilized Antigen Panning

The phage display anti-Met antibody mutation library was propagated in *E. coli* XL-1 Blue cells. Phage stocks were purified from culture surpernatants by precipitation with a saline polyethylene glycol solution and resuspended in PBS ($\sim 10^{13}$ phages/ml). Cell screening was then performed using S114 cells as a positive binding control and NIH 3T3 cells as a negative control. A total of five rounds of selection on NIH 3T3 and S114 live cells and 2 rounds on immobilized recombinant c-Met antigen were performed and 60 individual clones were selected for phage propagation. Of the 60 clones, 46 showed significant binding to Met, determined by an absorbance value 2 times higher than the irrelevant phage control (data not shown).

The use of the Met transfected cell line S114 in the multiple screening procedures described above permitted eliminating from consideration those antibodies that were binding to irrelevant receptors, enhancing enrichment ratios, and allowing the feasible selection of internalized antibody fragments. After seven rounds of selection, individual clones were analyzed by phage enzyme-linked immunosorbant assay (ELISA) to identify specific anti-Met that were defined as clones exhibiting ELISA signals at least fivefold greater on c-Met coated plates in comparison with signals on plates coated with an irrelevant antigen, bovine serum albumin (BSA). This phage library pool after seven rounds of sorting contained 84.4% positive clones (P/N>2.5). DNA sequence of 28 positive clones with high $OD_{450}$ value ($OD_{450}$>0.7, P/N>5) revealed 4 unique sequences.

Example 4

Sequence Analysis of Met-Binding Clones

A total of 28 scFvs were selected for further study. Nucleotide sequence analysis showed that these 28 binders represented 4 different scFv antibodies S1-S4 (Table 1). Amino acid sequences deduced from the nucleotide sequences showed four substitutions in L-CDR2 and two in L-CDR3, whereas there was only one substitution in CDR-H1 and four in CDR-H2 and CDR-H3. Close inspection of the CDR-H2 regions of 4 clones unveiled a strong, position-dependent preference for basic amino acid residues: at position 58, Lys transferred into Arg in all 4 clones; in the CDR-H3 region, at its C-terminal boundary, 3 of 4 clones contain Asp and Tyr at position 104 and 105, but in S1 the mutation occurred including Asp to Leu (104) and Tyr to Ile (105). At the N-terminal boundary, 3 of 4 clones' sequences are Ala-Arg/Lys, but in S1, Ala-Arg sequence transferred into Ala-Ser. The framework 50 (GTT) had not been mutated in 4 clones. Table 1 shows CDR sequences of the light and heavy chains of anti-Met scFvs. In CDR-L2, at position 50, the small hydrophobic amino acids alanine was changed into non-charged polar amino acid Thr; residue L50 is frequently involved in antigen contact, according to the knowledge base. At position 51, non-polar amino acid Pro was observed in 3 of 4 clones, except S1 which a basic amino acid Arg instead of the Ala. In CDR-L3, 2 of 4 clones had been varied. At position 96, His changed into an acidic amino acid Glu in S2, but in S4, His transferred into a basic amino acid Lys.

TABLE 1

|    | CDR1 | CDR2    | CDR3      |
|----|------|---------|-----------|
| VH |      |         |           |
| S0 | SSYA | IWYDGSNK | ARDNWGFDY |
| S1 | SSYA | IWYDGSNR | ASQATEGLI |
| S2 | NDYT | IWYDGSNR | ARVSQNFDY |
| S3 | SSYA | IWYDGSNR | AKHGMSTDY |
| S4 | SSYA | IWYDGSNR | AKLPKTPDY |
| VL |      |         |           |
| S0 |      | AAS     | SYSTPH    |
| S1 |      | TRS     | SYSTPH    |
| S2 |      | GPR     | VPTPYE    |
| S3 |      | TPR     | SYSTPH    |
| S4 |      | APT     | LPLNSK    |

After selection with live cells and immobilized antigens, and twice washing with NH$_4$SCN for immobilized antigen panning, internalizing scFvs were obtained by recovering phages endocytosed by the Met-overexpressing cell line S114. Without stringent washing, more than 85% clones contained the truncated antibody gene fragments or plasmid DNA only (data not shown).

Example 5

ScFv Expression, Refolding, and Purification

Figure 2:
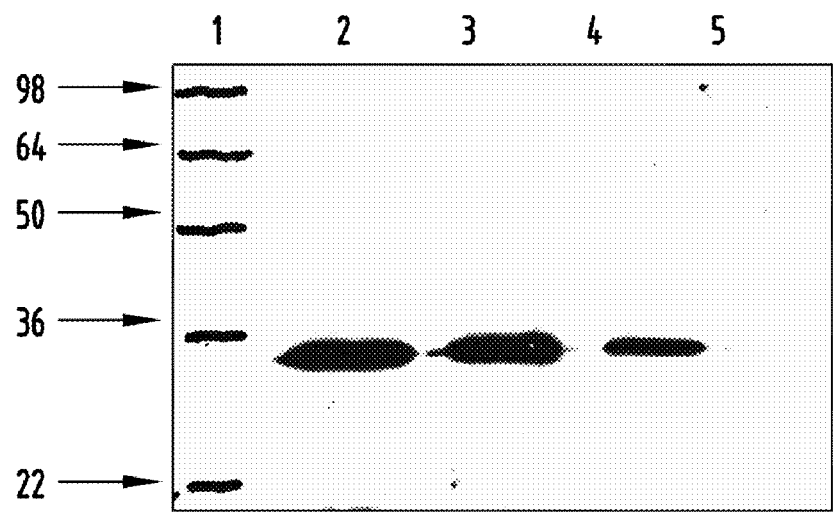
FIG. 2 is a Western blot confirming the expression of scFv in *E. Coli;*

ScFv were expressed in *E. coli* TOP10 induced by 0.02% L-arabinose as an inclusion body. After denaturing and refolding in Gu-HCl/Gluothine/L-arginine, scFv was purified by immotal metal-affinity chromatography (IMAC). One liter of the bacterial culture typically yielded approximately 20 mg of the final purified scFv product (FIG. 1). Different amounts of L-arabinose were used to induced the scFv expression, there were no prominent differences among the serial induction concentration from 2% to 0.02% at 37° C. The purified scFv was verified by SDS-PAGE and Coomesia staining, which showed a single band at about 34 kD (FIG. 2.). To verify the presence of the scFv found in SDS-PAGE, the purified protein was analyzed by Western blot. The *E. coli.* TOP10 whole protein was used as a negative control. As shown in FIG. 2, one positive band appeared at 34 kD position.

FIG. 1 shows a single chain antibody (scFv) expressed and purified IMAC (lane 1, standard molecular weight markers; lane 2 and 3 purified scFv protein). FIG. 2 shows a western blot analysis of scFv (lane 1, standard molecular weight marker, lane 2-4 purified scFv; lane 5, *E. coli* TOP10 protein as a negative control).

The conventional refolding procedures include rapid removal and dilution of the solubilizing substances. The solubilizing substances were removed rapidly by dialysis against GuHCl-free buffer with or without redox reagents resulting in less than 6% recovery from the total protein. Rapid dilution of the solubilized inclusion bodies in solution resulted in recovery of only a small mount of the functional scFv fragment (less than 15% from the total protein), although little aggregation was observed, indicating that non-functional or misfolded scFv had been produced. These results suggested that gradual removal of the solubilizing substances by using a continuous dialysis system might increase the efficiency of the recovery of biological activity (Baneyx, F., et al. (2004) *Nature Biotech.* 22: 1399-1408). In this study, GuHCl was removed step by step from 6M to 3M and then to 2 M, 1 M, 0.5 M and 0 M. the inventor added 375 um oxidized glutathione, 37.5 uM reduced glutathione and 400 mM in 1M and 0.5 M dialysis buffer. Thus, introducing temporary oxidizing conditions to the refolding stay may decelerate disulfide bond formation, resulting in a dramatically increased yield of functional scFv. L-arginine was added as a reagent that promotes preferential destabilization of wrongly folded structures to allow reshuffling of molecules trapped in non-productive side reactions.

Example 6

Characterization Analysis of the Selected Monoclonal scFv

Figure 3A:
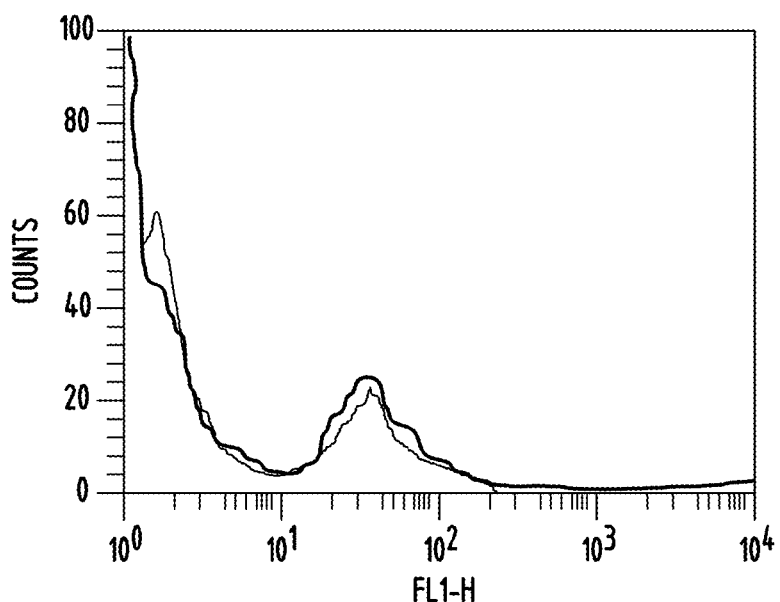
FIGS. 3A and 3B are graphs showing the binding affinity of scFv by FACS analysis.

To test the binding specificity, flow cytometry and immunoprecipation were carried out using S114, MKN45 and NIH 3T3 cell lines. Analysis of S114 cells incubated with scFv S1/anti-myc and FITC conjugated anti-mouse antibodies show a higher fluorescence intensity than NIH 3T3 cells (FIGS. 3A and 3B), and demonstrates S1 had a stronger binding ability and specificity to Met on the S114 cell surface.

FIG. 3 shows the binding ability of scFv as tested by FACS analysis, as follows: Graph A shows NIH 3T3 cells incubated with S1, anti-myc antibody and FITC-conjugated anti-mouse antibody (green line), or without only S1 (blue line); Graph B shows S114 cells incubated with S1, anti-myc antibody and FITC-conjugated anti-mouse antibody (red line), or without only S1 (green line).

Figure 4:
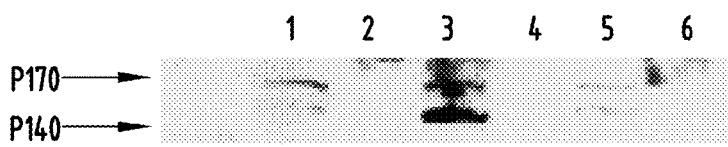
FIG. 4 is a Western blot of scFv-S1 that binds to Met.

Immunoprecipitation was carried out with S114, MKN45 and NIH 3T3. The results shown that both p170 precursor and mature p140 forms of Met were captured by S1 in S114 and MKN45 (c-Met positive cell lines; FIG. 4), but they were found in NIH 3T3 cells, which expressed very low levels of Met. This result illuminated further that anti-Met scFv could bind Met in its native form.

FIG. 4 shows immunoprecipitation and western blot analysis of S1. Met protein from cell extracts was immunoprecitated with S1 and detected by western blot analysis (lane 1: S114 lysate as a positive control; Lane 2, 3 and 5, NIH 3T3, MKN45 and S114 cell lysate immunoprecipitated with S1; lane 4 and 6, MKN45 and S114 cell lysate immunoprecipitated without S1).

Figure 5A:
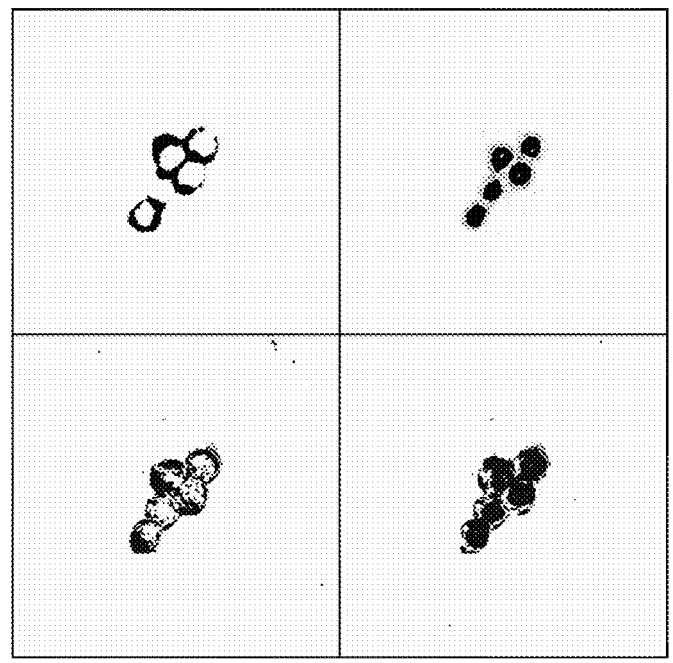
FIGS. 5A-5C are micrographs showing binding of scFv-S1 in S114 cells at 0.5, 1, and 2 hours.
Figure 5B:
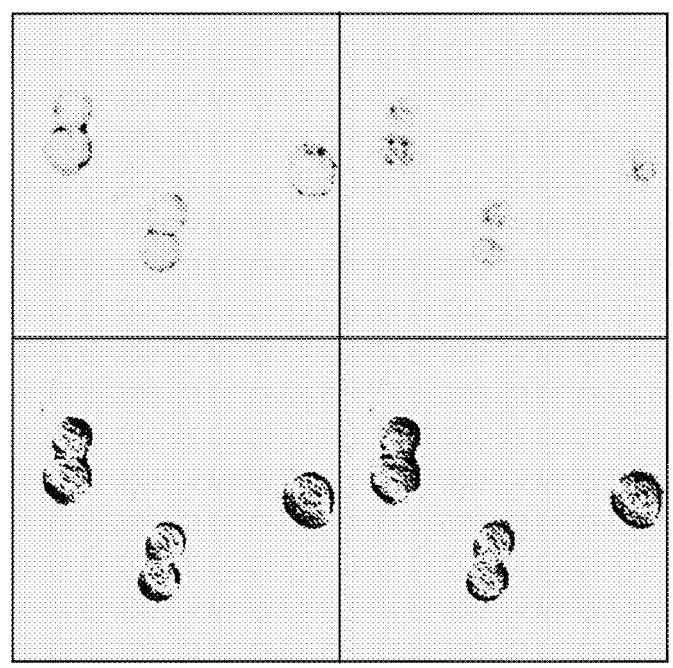
Figure 5C:
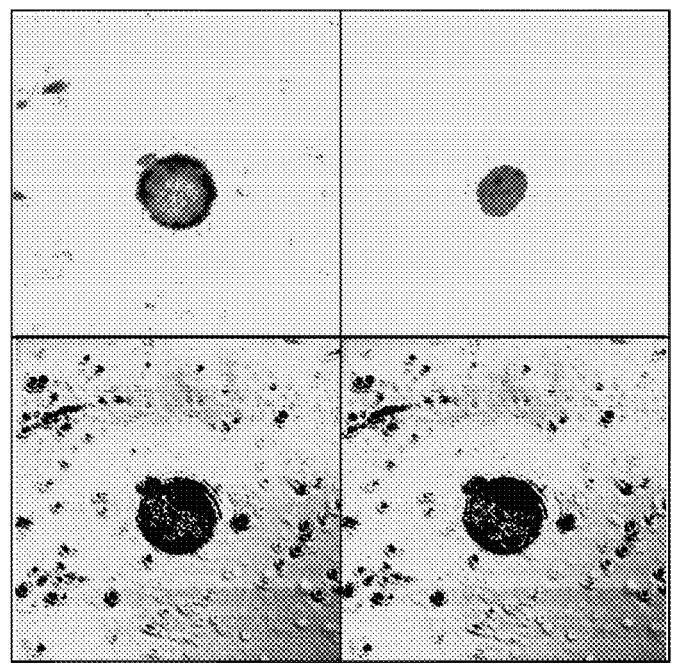

Since the phage antibodies were selected on the basis of internalization, the phage antibodies should be endocytosed by Met expressing cells. To confirm the binding specificity of S1 to bind the Met positive cells and to be internalized. Immunofluorescent staining of S114 cells treated with S1 phage for 0.5, 1 and 2 hr was detected with mouse anti-M13 antibody and FITC-conjugated anti-mouse IgG. The signals of phage were observed in the cytosol of 0.5-hr-treated cells, more signal occurred in 2-hr-treated cells, the amount of signal in the cytosol was dependent on the duration of the construct (FIGS. 5A-5C). The surface staining of S1 in S114 cells indicated that anti-Met scFv could bind Met in its native form and could be internalized. FIGS. 5A-5C shows immunofluorescent staining of S114 cells incubated with phage antibody (A, 0.5 hr; B, 1 hr; C, 2 hr).

To ensure the S1 binding to Met on the cell surface, double immunofluorescence staining was carried out with MKN45 cells (Met positive) and NIH 3T3 cells cultured in the same chamber wells. After incubation with MKN45 and NIH 3T3 cells, S1 which bound to the Met positive cell surface was detected by mouse anti-myc and Rhodamin conjugated anti-mouse IgG, meanwhile, the Met on S114 cell surface was detected by rabbit anti-Met and FITC conjugated anti-rabbit antibody.

Figure 6:
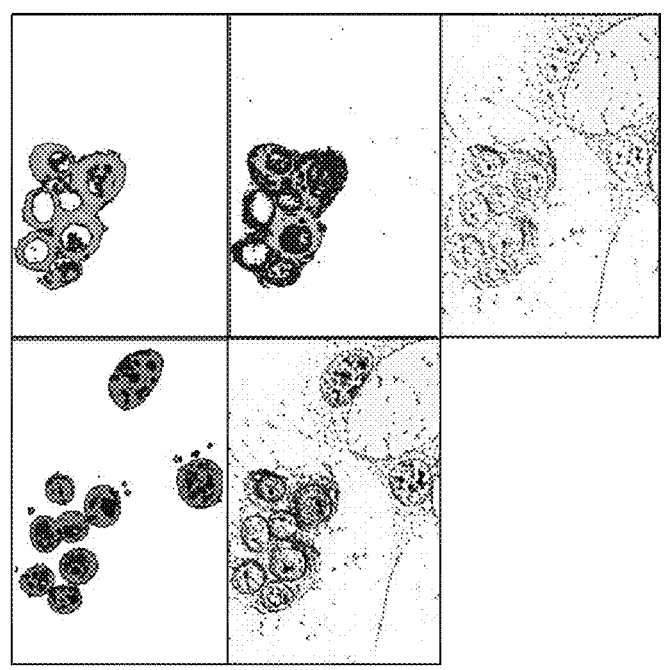
FIG. 6 is a micrograph showing co-localization of scFv-S1 on stained MKN45 and NIH 3T3 cells.

Fluorescence signals were detected by confocal laser fluorescence microscope. Stronger red and green fluorescence could be detected in the same areas on the surface of MKN45 cells, but very faint signals on NIH 3T3 cells (FIG. 6). This result demonstrated that S1 could bind the extracellular domain of Met (on the cell surface specifically). FIG. 6 shows co-localization detection of MKN45 and NIH 3T3 cells staining with S1/anti-myc antibody and rabbit anti-Met antibody, and Rhodamin-conjugated anti-mouse antibody and FITC-conjugated anti-rabbit antibody.

The affinity constant ($K_d$) of scFv-S1 which was measured by non-competitive ELISA using serial dilutions both of Met and scFv, had a value of $5.15 \times 10^{-8}$ mol/L which had been increased 117 times than the original Fab ($K_d = 6.04 \times 10^{-6}$ mol/L).

Because small phagemid genomes are more rapidly packaged than large ones, deleted phagemids will have an advantage following passage through the phage-packaged form. This becomes particularly obvious as detected phagemid forms are seen after multiple rounds of phage-based propagation when no functional selection for the displayed protein is applied (Lou, J., et al. (2001) *J. Immuno. Method*, 228:109-119; Heitner, T., et al. (2001) *J. Immunol. Methods*. 248: 17-30; Lou, J., et al. (2001) *J. Immuno. Method*, 228:109-119).

An analysis of mutant phage obtained after panning showed a variety of different sequences. In CDR-H2 at position 58, Lys mutated to Arg in 4 selected higher affinity clones, and demonstrated this amino acid is very important for antigen binding. In the Kabat database, the C-terminal boundaries of natural CDR-H3 sequences are not highly variable, but rather, usually contain either Phe-Asp-Tyr or Ala-Met-Asp-Tyr immediately preceding position 102. The result of this study shows that 3 of 4 clones contain Asp and Tyr at position 104 and 105, but in S1 the mutation occurred including Asp to Leu (position, 104) and Tyr to Ile (position, 105), and S1 is highest affinity clone. At the N-terminal boundary, sequences of 3 4 clones are Ala-Arg/Lys, but in S1, Ala-Arg sequence is transferred into Ala-Ser. The framework 50 (GTT) had not been mutated in 4 clones, even though the inventor designed a tailored mutation codon for GTT. This illuminated that crystal structure is more important than the general rule. If possible, to increase the library capacity is the key role in library construction and affinity maturation.

Anti-Met Fab generated from scFv could bind Met on cell surface specifically, but it is more stable than scFv. The advantages of working with a Fab are mostly related to the fact that this is a well-characterized protein fragment. Although the Fab was originally part of a larger molecular, in practice it functions well as an isolated unit. In addition, Fabs do not generally show a tendency to multimerize. Improvements in the affinity of a Fab are likely to result directly from improvements in intrinsic affinity of antibody combining site. A Fab can be converted to a whole antibody with a predictable maintenance of, or increase in, antigen affinity. The major disadvantage of Fabs relative to scFv is the generally lower expression levels in *E. coli*.

To date, most work has proceeded with the assumption that higher affinity antibodies, by virtue of prolonged tumor retention, will have superior tumor targeting and efficacy properties. This dogma was challenged many years ago by Weinstein et al, who proposed and demonstrated the existence of a binding site barrier that impedes the penetration of antibodies into tumor masses because durable, high-affinity interactions between the antibody and its target block the diffusion of such antibodies throughout the tumor mass (van Osdol, W., et al. (1991) *Cancer Res.* 51: 4776-4784; Weiner, L., et al. (2005) *Nature Biotech* 23, 556-557). This hypothesis was supported and extended several years ago by Adams et al (Gregory, A. et al. (2001) *Cancer Res.* 61: 4750-4755). A threshold affinity of $10^{-7}$-$10^{-8}$ M was required for specific tumor localization of scFv, and uptake reached a plateau at $10^{-9}$-$10^{-11}$ M. These data support the concept of a 'binding-site' barrier that can impair penetration of the tumor for very high-affinity antibodies. Gerwin Huls et al. experiments showed that the lower-affinity ($5 \times 10^{-7}$) huMab, BBS-54, demonstrated slightly more efficient tumor cell killing with peripheral blood mononuclear cells as a source of effect cells, whereas the higher-affinity ($2 \times 10^{-9}$) anti-tumor huMab more efficiently recruited complement factors. Moreover, the lower-affinity antibody more readily penetrated multicell spheroids of tumor cells (Huls, G., et al. (2001) *Intl Cancer Res.* 50, 163-171).

The affinity of antibodies can profoundly affect their ability to localize to tumors, and have no effect on uptake ratio. Paul Carter et al. showed that the molecular architecture of antibodies is readily modified to create non-natural antibody formats that vary in size and valency, with significant effects on tumor targeting ability. For example, a dimeric anti-erbB2 antibody fragment, (scFv')2, showed increased tumor uptake compared with a monomeric Fab fragment of similar size (~50 kDa), and presumed similar tumor penetration and pharmacokinetic properties (Weiner, L. et al. (2005) *Nature Biotech* 23, 556-557). The inventor found antibody uptake ratio had no relation with affinity. In three internalized Fab antibodies, the Fab with $10^{-6}$ M affinity has the highest uptake ratio compared to other two Fabs with $10^{-8}$M and $10^{-9}$ M affinity value.

Example 7

Figure 3B:
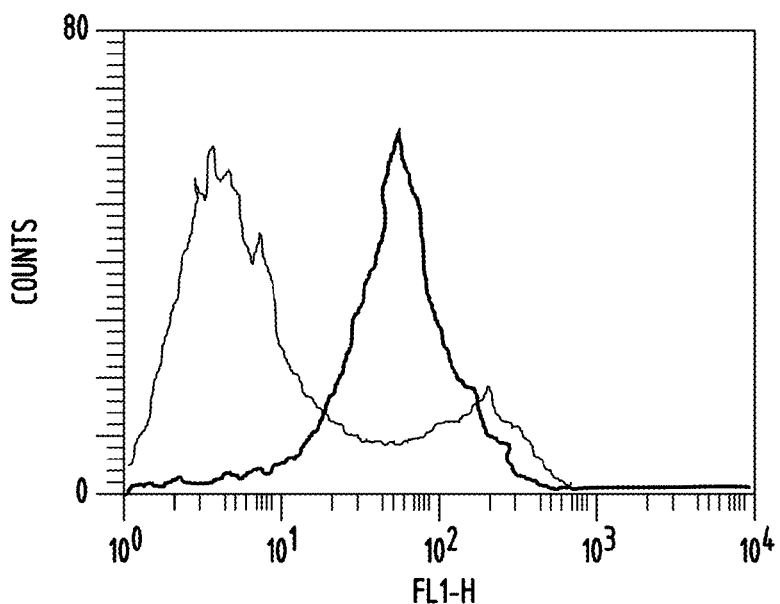
Figure 7A:
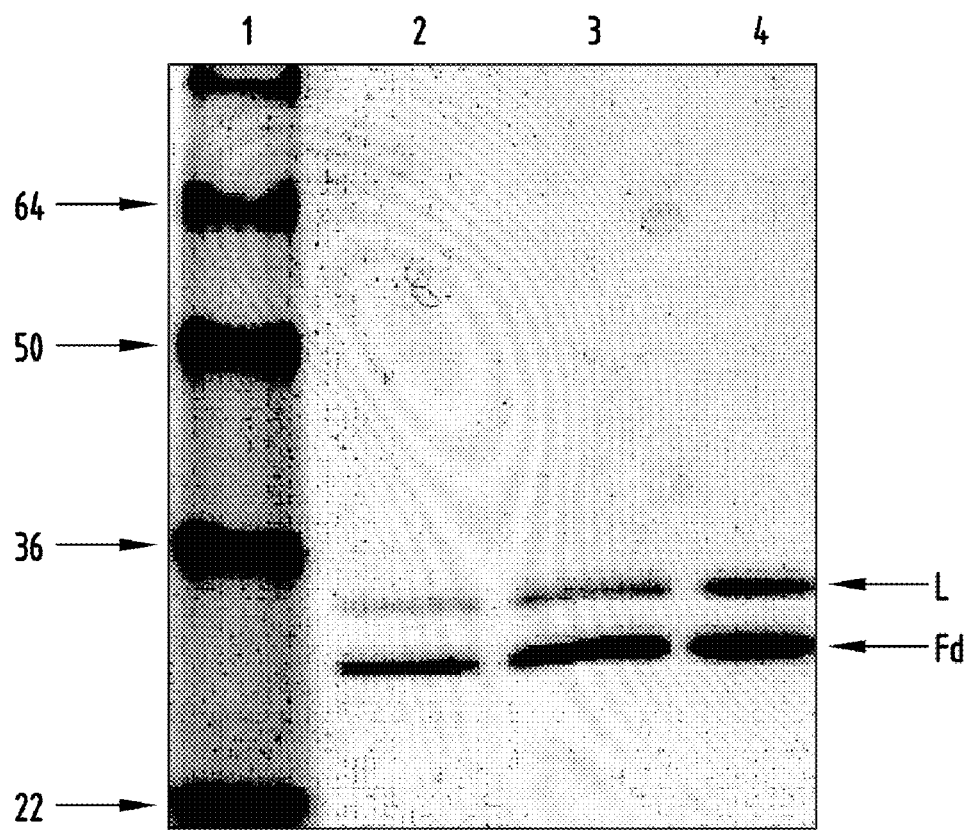
FIGS. 7A and 7B are a Coomesia staining and a Western blot of purified Fab-Met-2, respectively.
Figure 7B:
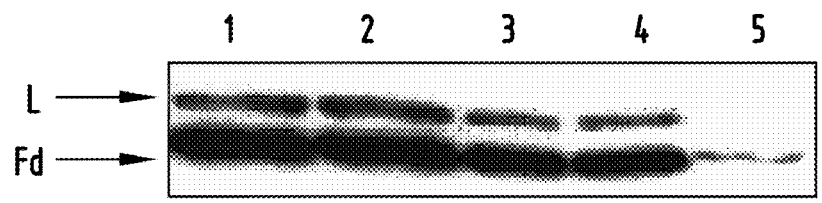

Fab Expression and Purification pCom3XSS-Fab ligation was used to transform into TOP10F', a non suppression *E. coli* strain. Single colony of transformant was picked and used to inoculate SB medium containing 100 µg/ml carbenicillin with 2% glucose for soluble Fab expression. Soluble Fab was purified by ImmunoPure Immobilized Protein L in FPLC system. One liter of the bacterial culture typically yielded approximately 1 mg of the final purified Fab product. The purified Fab was verified by SDS-PAGE and coomassie staining, which showed two bands at about 25 kD and 27 kD (FIGS. 7A and 7B.). To verify the presence of the Fab which found in SDS-PAGE, the purified protein was analyzed by western blot. As shown in FIG. 3B, two positive bands appeared at the expected positions.

FIGS. 7A and 7B shows an SDS-PAGA and Western blot analysis of purified Fab. (A) shows Fab coomassie staining, lane 1, standard molecule weight marker, lane 2-4, Fab; (B) shows Western blot of Fab: lane1, Fab expressed in SB for 6 hrs, lane2, Fab expressed in SB for 12 hrs, lane3, Fab expressed in LB for 6 hrs: lane 4, Fab expressed in LB for 12 hrs and lane5, Fab expressed in SB for 6 hrs without resuspension.

Example 8

Cytotoxicity Assay in vitro

The first step was to demonstrate the effect of varying ratio of a saporin conjugated anti-human antibody (Hum-ZAP), a protein synthesis cessation reagent, to anti-Met Fab. Hum-ZAP is used as a secondary immunotoxin that eliminates the need to couple every candidate antibody to the toxin because it can simply be added to cells in culture with the antibody of interest. The results showed the effect when Hum-ZAP was diluted as 100 ng/well against 100 ng anti-Met Fab was better than others. A stoichiomeric effect was also seen: as the number of anti-Met Fab increased relative to Hum-ZAP molecules, fewer cells were eliminated. Increased levels of free anti-Met Fab, caused the ratio of Hum-ZAP+ Fab complexes to free Fab to decrease. More free Fab and fewer Fab+ Hum-ZAP complexes bound the cells and were internalized. For Met negative cell line NIH 3T3, there was no significant variation among the different amount of Fab and Hum-ZAP incubated for 96 hrs.

Figure 8:
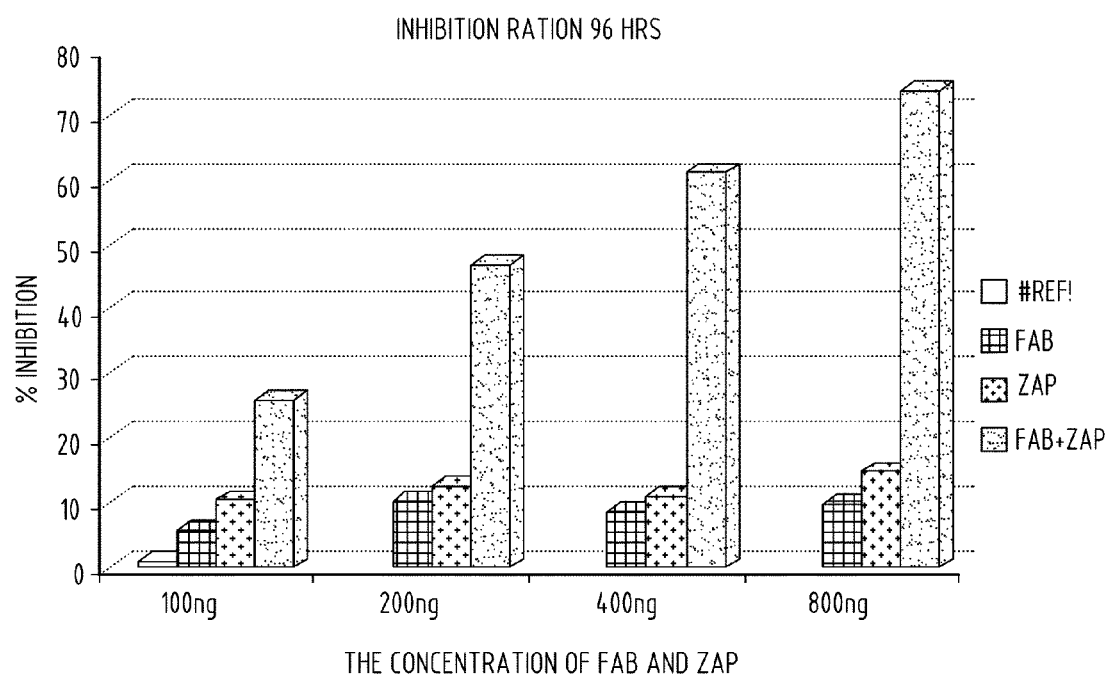
FIG. 8 is a graph showing the inhibition ratio of protein synthesis in S114 cells of varying concentrations of Fab and Hum-ZAP in 96 hours.
Figure 9:
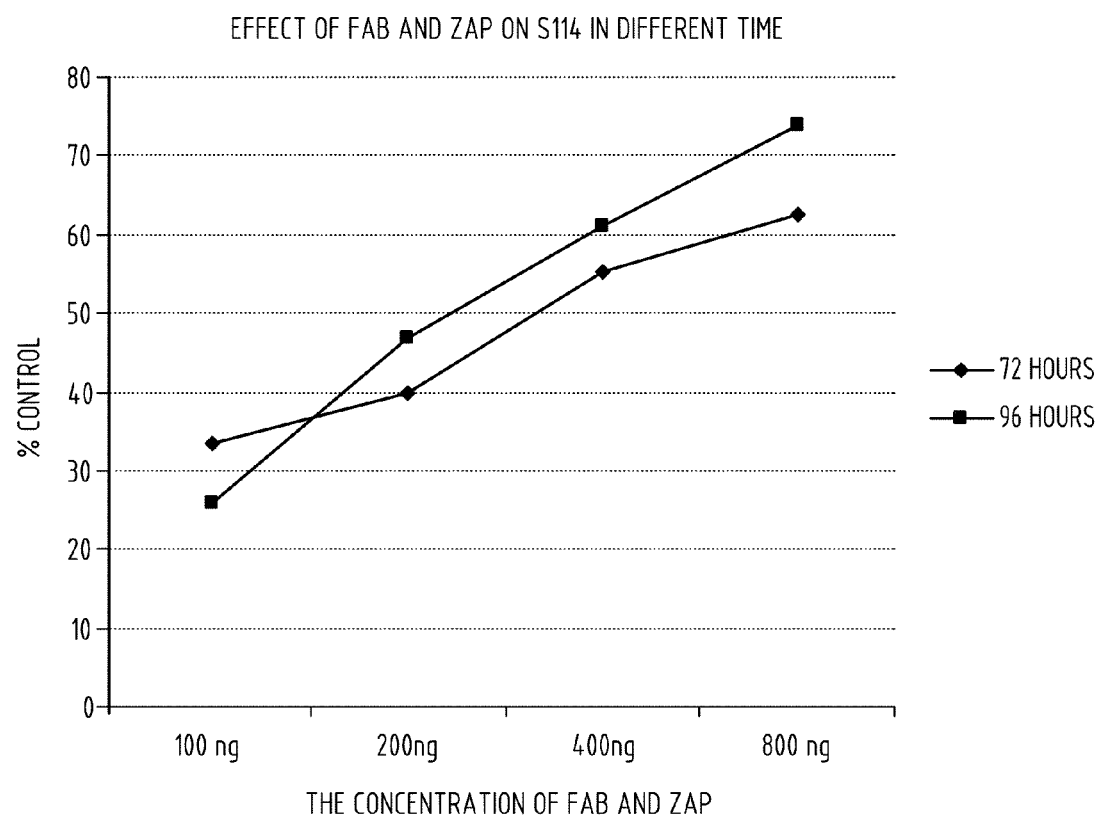
FIG. 9 is a graph showing the inhibition ratio of protein synthesis in S114 cells of varying concentrations of Fab and Hum-ZAP in 72 and 96 hours.

By itself, Hum-ZAP was not internalized at working concentration. This fact is significant because no activation was necessary for the Hum-ZAP molecule to stop protein synthesis, only internalization so that the saporin had access to the cellular ribosomes. The results showed significant cell death occurs only above 100 ng/well of Hum-ZAP and 100 ng human Fab fragments. The inhibition ratios increased after cells were incubated with Fab and Hum-ZAP in 72 hrs and 96 hrs (FIGS. 8 and 9).

Figure 10:
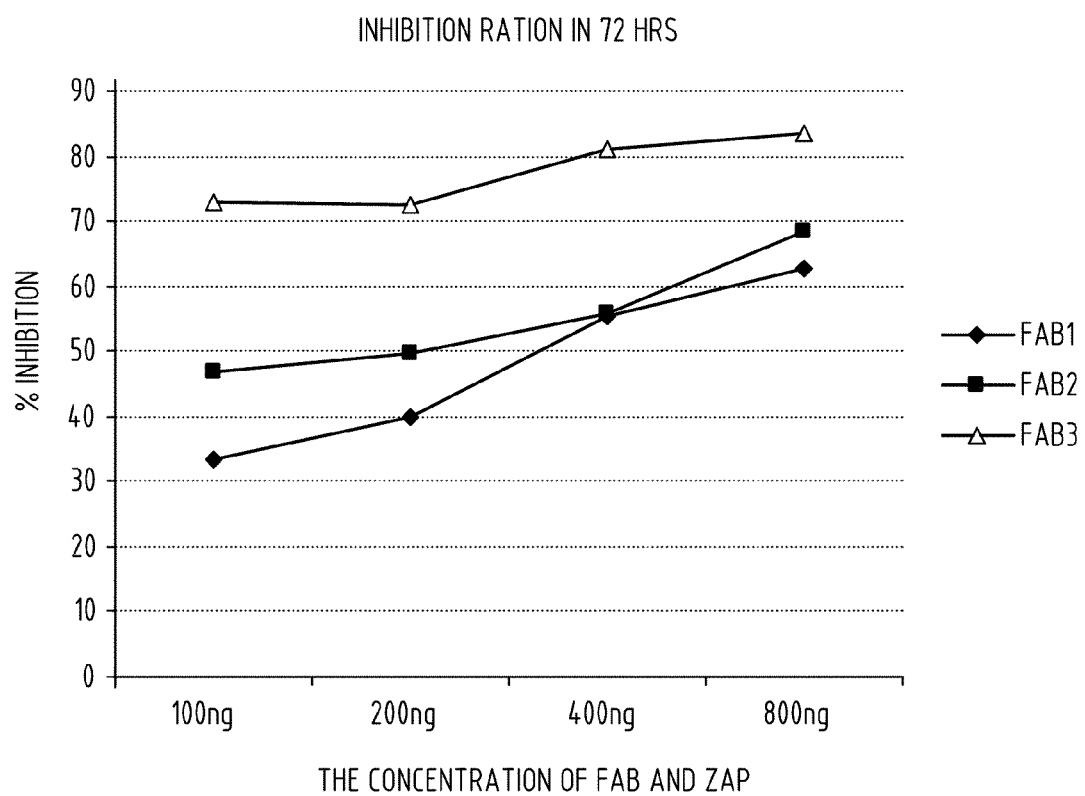
FIG. 10 is a graph showing the inhibition ratio on S114 cells of three Fabs (1-3) and Hum-ZAP.

Comparing three Fabs with different affinity values, the lowest affinity Fab ($10^{-6}$M) has the highest protein synthesis inhibition ratio as compared to the two others with affinities of $10^{-8}$ M and $10^{-9}$ M. This result demonstrated that the antibody uptake ration was independent of the antibody affinity. In the absence of an anti-Met Fab, just a few Hum-ZAP was internalized at high concentration above 800 ng/well (FIG. 10).

Among the anti-Met Fab fragments captured from the same CDR mutation library with similar frameworks and some different amino acids in CDRs, only two Fabs could be internalized by Met over-expressed cell S114.

Having now fully described this invention, it will be appreciated by those skilled in the art that based upon the teachings herein, the same can be performed within a wide range of equivalent parameters, concentrations, and conditions without departing from the spirit and scope of the invention and without undue experimentation. Thus, changes and modifications may be made without departing from this subject matter described herein and its broader aspects and, therefore, the appended claims are to encompass within their scope all such changes and modifications as are within the true spirit and scope of this subject matter described herein.

What is claimed is:

1. A monoclonal antibody, or antigen-binding fragment thereof, against receptor protein tyrosine kinase Met (Met), comprising an antibody or fragment produced either by the bacterial strain deposited in the American Type Culture Collection under Patent Deposit Designation ATCC PTA-7897 or by the bacterial strain deposited in the American Type Culture Collection under Patent Deposit Designation ATCC PTA-7898.

2. The monoclonal antibody or antigen-binding fragment of claim 1 wherein an imaging agent is conjugated to said monoclonal antibody or antigen-binding fragment.

3. The monoclonal antibody or antigen-binding fragment of claim 1 wherein a drug is conjugated to said monoclonal antibody or antigen-binding fragment.

4. The monoclonal antibody or antigen-binding fragment of claim 3 wherein said drug is a chemotherapeutic.

5. A composition comprising an anti-receptor protein tyrosine kinase Met (Met) Fab or scFv produced by the bacterial strain deposited in the American Type Culture Collection under Patent Deposit Designation ATCC PTA-7897 or by the bacterial strain deposited in the American Type Culture Collection under Patent Deposit Designation ATCC PTA-7898, respectively.

6. The composition of claim 5 wherein an imaging agent is conjugated to said anti-Met Fab or scFv.

7. The composition of claim 5 wherein a drug is conjugated to said Fab or scFv.

8. The composition of claim 7 wherein said drug is a chemotherapeutic.

9. A human monoclonal antibody or antigen-binding fragment that binds specifically to receptor protein tyrosine kinase Met (Met) wherein said monoclonal antibody or antigen-binding fragment comprises a light chain variable region having the amino acid sequence of SEQ ID No. 3 and a heavy chain variable region having the amino acid sequence of SEQ ID No. 4.

10. A human monoclonal antibody or antigen-binding fragment thereof that binds specifically to receptor protein tyrosine kinase Met (Met) wherein the monoclonal antibody or antigen-binding fragment comprises the amino acid sequence of SEQ ID No. 6.

11. A method for detecting the level of Met expression in a cell, wherein Met is a receptor protein tyrosine kinase, comprising
administering to a cell the monoclonal antibody, antigen-binding fragment
thereof, or composition of any of claim 1, 5, 9, or 10, and detecting the level of Met expression in the cell.

12. The method of claim 11 wherein said monoclonal antibody or antigen-binding fragment is conjugated to an imaging agent.

13. An isolated cell line that produces the monoclonal antibody or antigen-binding fragment of claim 9 or 10.

14. The isolated cell line of claim 13 which is the bacterial strain deposited in the American Type Culture Collection under Patent Deposit Designation ATCC PTA-7897 or the bacterial strain deposited in the American Type Culture Collection under Patent Deposit Designation ATCC PTA-7898.

15. A method for producing an anti-Met antibody or antigen-binding fragment thereof, comprising culturing the cell line according to claim 13 under suitable conditions and recovering said monoclonal antibody or antigen-binding fragment.

16. A kit, comprising: a first container, a label on said container, and a composition contained within said container, wherein the composition includes an active agent, the label on said container indicates the use of the composition, and the active agent in said composition comprises the monoclonal antibody or an antigen-binding fragment according to any of claim 1, 9, or 10; a second container comprising a pharmaceutically-acceptable buffer; and instructions for using the monoclonal antibody or antigen-binding fragment thereof.

17. The monoclonal antibody or antigen-binding fragment of claim 9 wherein an imaging agent is conjugated to said monoclonal antibody or antigen-binding fragment.

18. The monoclonal antibody or antigen-binding fragment of claim 9 wherein a drug is conjugated to said monoclonal antibody or antigen-binding fragment.

19. The monoclonal antibody or antigen-binding fragment of claim 18 wherein said drug is a chemotherapeutic.

20. The monoclonal antibody or antigen-binding fragment of claim 10 wherein an imaging agent is conjugated to said monoclonal antibody antigen-binding fragment.

21. The monoclonal antibody or antigen-binding fragment of claim 10 wherein a drug is conjugated to said monoclonal antibody or antigen-binding fragment.

22. The monoclonal antibody or antigen-binding fragment of claim 21 wherein said drug is a chemotherapeutic.

* * * * *

SEQUENCE LISTING

<160> NUMBER OF SEQ ID NOS: 6

<210> SEQ ID NO 1
<211> LENGTH: 657
<212> TYPE: DNA
<213> ORGANISM: homo sapiens

<400> SEQUENCE: 1

```
gagctccaga tgacccagtc tccatcctta ctctctgcat ctacaggaga cagagtcacc      60
atcagttgtc gggcaagtca gagcattagc agctatttaa attggtatca gcagaaacca     120
gggaaagccc ctaagctcct gatctatact cggagcagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctcacac ttttggccag     300
gggaccaagc tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacctgacg      540 ctgagcaaag cagactacga gaaacacaaa gtctacgcct gcgaagtcac ccatcagggc     600
ctgagcttgc ccgtcacaaa gagcttcaac aggggaagag tgttagttct agataat        657
```

<210> SEQ ID NO 2
<211> LENGTH: 669
<212> TYPE: DNA
<213> ORGANISM: homo sapiens

<400> SEQUENCE: 2

```
gaggtgcagc tggtggagtc tggcggaggc gtggtccagc ctggggaggtc cctgagactc     60 tcctgtgcag cctctggatt caccttcagt agctatgcta tgcactgggt ccgccaggct    120
ccaggcaagg ggctggagtg ggtggcagtt atatggtatg atggaagtaa tagatactat    180
gcagactccg tgaagggccg attcaccatc tccagagaca attccaagaa cacgctgtat    240
ctgcaaatga acagcctgag agccgaggac acggctgtgt attactgtgc gagccaagct    300
```

-continued

```
actgaaggac taatttgggg ccagggcacc ctggtcaccg tctcccctgc ctccaccaag    360
ggcccatcgg tcttcccct  ggcacctcc  tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaagg ttgagcccaa atcttgtgac    660
aaaactagt                                                            669
```

```
<210> SEQ ID NO 3
<211> LENGTH: 219
<212> TYPE: PRT
<213> ORGANISM: homo sapiens

<400> SEQUENCE: 3
```

Glu Leu Gln Met Thr Gln Ser Pro Ser Leu Leu Ser Ala Ser Thr Gly
1               5                   10                  15

Asp Arg Val Thr Ile Ser Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Thr Arg Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro His
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Leu Pro Val Thr Lys Ser
        195                 200                 205

Phe Asn Arg Gly Arg Val Leu Val Leu Asp Asn
    210                 215

```
<210> SEQ ID NO 4
<211> LENGTH: 223
<212> TYPE: PRT
<213> ORGANISM: homo sapiens

<400> SEQUENCE: 4
```

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Trp Tyr Asp Gly Ser Asn Arg Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Gln Ala Thr Glu Gly Leu Ile Trp Gly Gln Gly Thr Leu Val
                100                 105                 110

Thr Val Ser Pro Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr Ser
    210                 215                 220

<210> SEQ ID NO 5
<211> LENGTH: 723
<212> TYPE: DNA
<213> ORGANISM: homo sapiens

<400> SEQUENCE: 5
gagctccaga tgacccagtc tccatcctta ctctctgcat ctacaggaga cagagtcacc    60
atcagttgtc gggcaagtca gagcattagc agctatttaa attggtatca gcagaaacca   120
gggaaagccc ctaagctcct gatctatact cggagcagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctcacac ttttggccag   300
gggaccaagc tggagatcaa aggtggttcc tctagatctt cctcctctgg tggcggtggc   360
tcgggcggtg gtgggaggt gcagctggtg gagtctggcg aggcgtggt ccagcctggg   420
aggtccctga ctctcctg tgcagcctct ggattcacct tcagtagcta tgctatgcac   480
tgggtccgcc aggctccagg caaggggctg gagtgggtgg cagttatatg gtatgatgga   540
agtaatagat actatgcaga ctccgtgaag ggccgattca ccatctccag agacaattcc   600
aagaacacgc tgtatctgca aatgaacagc ctgagagccg aggacacggc tgtgtattac   660
tgtgcgagcc aagctactga aggactaatt tggggccagg gcaccctggt caccgtctcc   720
cct                                                                 723

<210> SEQ ID NO 6
<211> LENGTH: 241
<212> TYPE: PRT
<213> ORGANISM: homo sapiens

<400> SEQUENCE: 6

Glu Leu Gln Met Thr Gln Ser Pro Ser Leu Leu Ser Ala Ser Thr Gly
 1               5                  10                  15

Asp Arg Val Thr Ile Ser Cys Arg Ala Ser Gln Ser Ile Ser Ser Tyr

-continued

```
                    20                  25                  30
Leu Asn Trp Tyr Gln Gln Lys Pro Gly Lys Ala Pro Lys Leu Leu Ile
            35                  40                  45

Tyr Thr Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                      70                  75                  80

Glu Asp Phe Ala Thr Tyr Tyr Cys Gln Gln Ser Tyr Ser Thr Pro His
                85                  90                  95

Thr Phe Gly Gln Gly Thr Lys Leu Glu Ile Lys Gly Gly Ser Ser Arg
                100                 105                 110

Ser Ser Ser Ser Gly Gly Gly Ser Gly Gly Gly Gly Glu Val Gln
            115                 120                 125

Leu Val Glu Ser Gly Gly Gly Val Val Gln Pro Gly Arg Ser Leu Arg
        130                 135                 140

Leu Ser Cys Ala Ala Ser Gly Phe Thr Phe Ser Ser Tyr Ala Met His
145                     150                 155                 160

Trp Val Arg Gln Ala Pro Gly Lys Gly Leu Glu Trp Val Ala Val Ile
                165                 170                 175

Trp Tyr Asp Gly Ser Asn Arg Tyr Tyr Ala Asp Ser Val Lys Gly Arg
                180                 185                 190

Phe Thr Ile Ser Arg Asp Asn Ser Lys Asn Thr Leu Tyr Leu Gln Met
            195                 200                 205

Asn Ser Leu Arg Ala Glu Asp Thr Ala Val Tyr Tyr Cys Ala Ser Gln
        210                 215                 220

Ala Thr Glu Gly Leu Ile Trp Gly Gln Gly Thr Leu Val Thr Val Ser
225                 230                 235                 240

Pro
```